US012281158B2

(12) United States Patent
Suzuki et al.

(10) Patent No.: US 12,281,158 B2
(45) Date of Patent: Apr. 22, 2025

(54) PROPHYLACTIC AND/OR THERAPEUTIC AGENT OF INFECTIOUS DISEASES OR INFLAMMATORY DISEASES

(71) Applicants: A-CLIP Institute, Co., Ltd., Chiba (JP); National Institutes of Biomedical Innovation, Health and Nutrition, Ibaraki (JP)

(72) Inventors: Kazuo Suzuki, Chiba (JP); Yosuke Kameoka, Chiba (JP); Yoshio Yamakawa, Chiba (JP); Fukuko Kishi, Chiba (JP); Osamu Suzuki, Ibaraki (JP); Minako Koura, Ibaraki (JP); Junichiro Matsuda, Ibaraki (JP)

(73) Assignees: A-CLIP INSTITUTE, CO., LTD., Chiba (JP); NATIONAL INSTITUTES OF BIOMEDICAL INNOVATION, HEALTH AND NUTRITION, Osaka (JP)

( * ) Notice: Subject to any disclaimer, the term of this patent is extended or adjusted under 35 U.S.C. 154(b) by 355 days.

(21) Appl. No.: 17/655,687

(22) Filed: Mar. 21, 2022

(65) Prior Publication Data

US 2022/0213180 A1 Jul. 7, 2022

Related U.S. Application Data

(62) Division of application No. 16/481,241, filed as application No. PCT/JP2018/002576 on Jan. 26, 2018, now abandoned.

(30) Foreign Application Priority Data

Jan. 27, 2017 (JP) .................................. 2017-013486

(51) Int. Cl.
C07K 16/18 (2006.01)
A61K 39/00 (2006.01)
A61K 49/00 (2006.01)
G01N 33/50 (2006.01)

(52) U.S. Cl.
CPC .......... *C07K 16/18* (2013.01); *A61K 49/0008* (2013.01); *G01N 33/5088* (2013.01); *A61K 2039/505* (2013.01); *C07K 2317/622* (2013.01); *C07K 2317/76* (2013.01); *G01N 2333/775* (2013.01)

(58) Field of Classification Search
CPC ............................ C07K 16/18; C07K 2317/76
See application file for complete search history.

(56) References Cited

U.S. PATENT DOCUMENTS

| 10,208,131 B2 | 2/2019 | Suzuki |
| 2003/0022330 A1 | 1/2003 | Bartel et al. |
| 2010/0129919 A1 | 5/2010 | Levin et al. |
| 2010/0286025 A1 | 11/2010 | Anantharamaiah et al. |
| 2013/0164290 A1 | 6/2013 | Suzuki |
| 2015/0166645 A1 | 6/2015 | Suzuki |
| 2016/0245815 A1 | 8/2016 | Sanada et al. |

FOREIGN PATENT DOCUMENTS

| CN | 105637366 A | 6/2016 |
| EP | 3054298 A1 | 8/2016 |
| JP | H05-304989 A | 11/1993 |
| JP | 2000-14383 A | 1/2000 |
| JP | 2004-81199 A | 3/2004 |
| JP | 2010-517007 A | 5/2010 |
| JP | 2013-147495 A | 8/2013 |
| JP | 2016-160265 A | 9/2016 |
| WO | WO2008115518 A2 * | 9/2008 |
| WO | 2009/044723 A1 | 4/2009 |
| WO | 2011143308 A2 | 11/2011 |
| WO | 2012/039161 A1 | 3/2012 |
| WO | 2015/050107 A1 | 4/2015 |
| WO | 2016/121695 A1 | 8/2016 |
| WO | 2016/140210 A1 | 9/2016 |

OTHER PUBLICATIONS

Poggioli et al., "Infliximab in the treatment of Crohn's disease," Therapeutics and Clinical Risk Management (2007); 3(2):301-308.
Watts et al., "Vasculitis and inflammatory arthritis," Best Practice & Research Clinical Rheumatology (2016); 30:916-931.
Goeken, "AntiNeutrophil Cytoplasmic Antibody—A Useful Serological Marker for Vasculitis," Journal of Clinical Immunology (1991); 11(4):161-174.
Suzuki et al., "A novel autoantibody against moesin in the serum of patients with MPO-ANCA-associates vasculitis," Nephrology Dialysis Transplantation (2014); 29:1168-1177.
Carney, "Potential role of an anti-moesin autoantibody in MPO-AAV," Nature Reviews Nephrology (2014); 10(65).
Ito-Ihara et al., "Clinical Efficacy of Intravenous Immunoglobulin for Patients with MPO-ANCA-Associated Rapidly Progressive Glomerulonephritis" Nephron Clinical Practice (2006); 102:c35-c42.
Unizony et al., "Clinical outcomes of treatment of anti-neutrophil cytoplasmic antibody (ANCA)-associates vasculitis based on ANCA type," Ann Rhuem Dis (2015); 0:1-4.

(Continued)

*Primary Examiner* — Brian Gangle
*Assistant Examiner* — Lakia J Jackson-Tongue
(74) *Attorney, Agent, or Firm* — FOX ROTHSCHILD LLP

(57) ABSTRACT

[Problem] To provide a therapeutic method specialized for an inflammatory disease such as intractable vasculitis and an infectious disease, which is different from the previous therapeutic methods, in which a target molecule was not determined, by determining the target molecule useful for treating these diseases.
[Solution] According to one aspect of the present invention, a prophylactic and/or therapeutic agent for an infectious disease or an inflammatory disease which contains an antibody recognizing apolipoprotein A2 (APOA2) as an active ingredient is provided.

7 Claims, 17 Drawing Sheets

Specification includes a Sequence Listing.

(56) References Cited

OTHER PUBLICATIONS

De Joode et al., "Performance of two strategies for urgent ANCA and anti-GBM analysis in vasculitis," European Journal of Internal Medicine (2014); 25:182-186.
Kallenberg et al., "Autoantibodies vex the vasculature," Nature Medicine (2008); 14(10):1018-1019.
Kain et al., "Molecular mimicry in pauci-immune focal necrotizing glomerulonephritis," Nature Medicine (2008); 14(10):1088-1096.
Tomizawa et al., "Reduction of MPO-ANCA epitopes in SCG/Kj mice by 15-deoxyspergualin treatment restricted by IgG2b associates with crescentic glomerulonephritis," Rheumatology (2010); 49:1245-1256.
Cleveland Clinic; "Why You Should Pay Attention to Chronic Inflammation", Oct. 14, 2014, Cancer Care https://health.clevelandclinic.org/why-you-should-pay-attention-to-chronic-inflammation/.
Han Seunggu: "Understanding and Managing Chronic Inflammation", Heathline.com, https://www.healthline.com/health/chronic-inflammation#:~:text=inflammation%20refers%20to%20your%20body's,response%20from%20your%20immune%20system, Year: 2020.
Johns Hopkins Vasculitis Center: "Vasculitis Frequently Asked Questions", https://www.hopkinsvasculitis.org/resources/vasculitis-faq/, pp. 1-11, Year: 2020.
Centers for Disease Control and Prevention: "How to Protect Yourself & Ohter Protect Yourself", https://www.cdc.gov/coronavirus/2019-ncov/prevent-getting-sick/prevention.html (Year: 2020).
Oharaseki, et al: "Administration of Recombinant Single Chain Fragment of Variable Region (hScFv) of IgG Suppresses Development of Murine Vasculitis Induced with Candida Albicans Water-Soluble Fraction: An Animal Model of Kawasaki Disease", ADC Letter for Infectious Disease Control, Jul. 2019, vol. 6, No. 2, pp. 51-55.
Kameoka, et al: "Establishment of a Library Having 204 Effective Clones of Recombinant Single Chain Fragment of Variable Region (hScFv) of IgG for Vasculitis Treatment", ADC Letter for Infectious Disease Control, Jul. 2017, vol. 4, No. 2, pp. 44-47.
Brown, et al: "Tolerance to Single, but Not Multiple, Amino Acid Replacements in Antibody VH CDR2, A Means of Minimizing B Cell Wastage from Somatic Hypermutation", Journal of Immunology, 1996; 156(9):3285-3291.
Vajdos, et al: "Comprehensive Functional Maps of the Antigen-binding Site of an Anti-ErbB2 Antibody Obtained with Shotgun Scanning Mutagenesis", Journal of Molecular Biology, 2002; 320(2):415-428 at 416.
Harding, et al: "The immunogenicity of humanized and fully human antibodies, Residual immunogenicity resides in the CDR regions", mAbs, 2010; 2(3): 256-265.
Office Action dated Sep. 19, 2022 issued in Chinese Applicatioin No. 201880008834.3 (18 pages).

* cited by examiner

Proteins recognized by VasSF was identified by proteome analysis

Identification of target protein by database search

Solvent

APOA2

Enlarged figures

Solvent        APOA2

Spleen

Lung

PROPHYLACTIC AND/OR THERAPEUTIC AGENT OF INFECTIOUS DISEASES OR INFLAMMATORY DISEASES

CROSS-REFERENCE TO RELATED APPLICATION

The present application is a Divisional of U.S. Nonprovisional patent application Ser. No. 16/481,241, filed Jul. 26, 2019, which is the U.S. National Phase of International Patent Application Serial No. PCT/JP2018/002576, filed Jan. 26, 2018, which claims the benefit of priority of Japanese Patent Application No. 2017-013486, filed Jan. 27, 2017. The entire disclosures of the applications noted above are incorporated herein by reference.

REFERENCE TO AN ELECTRONIC SEQUENCE LISTING

This application contains a Sequence Listing which has been submitted electronically in ASCII format and is hereby incorporated by reference in its entirety. Said file, created on Sep. 4, 2024, is named SeqList2-037462-00058.txt and is 9,614 bytes in size.

TECHNICAL FIELD

This invention is about agents for prophylaxis and/or therapy for infectious diseases or inflammatory diseases.

BACKGROUND ART

Antibody drugs (Infliximab, Actemura, etc.) have been used for rheumatoid arthritis and related diseases which is an inflammatory disease. On the other hand, the use of steroids and antibody drugs has been studied as there is no standard therapeutic agents for an intractable vasculitis which is a similar inflammatory disease. Recently, immunoglobulin (ig) drugs have been used in intractable vasculitis, eosinophilia granulomatosis with polyangiitis: EGPA Churg-Strauss syndrome. The immunoglobulin is a generic term of a protein structurally and/or functionally related to antibodies. In other words, an immunoglobulin, which binds to its specific antigens, is defined as antibody corresponding to specific antigens.

As drugs for intractable vasculitis, steroids are suggested by Guideline, and antibody drugs have been studied to be used in standard treatments. Infliximab which has been used as an antibody medicine for a specific antigen as a drug for (Remicade®; i.e., Infliximab) is an antibody to antigen an inflammatory cytokine TNF-alpha. It has been developed for an antibody drug to suppress over-produced TNF-alpha in Crohn's disease. Infliximab is an antibody drug that also destroys cells producing TNF alpha (non-patent document-1). On the other hand, Rizximab (Rizane) has been developed for lymphoma treatment as a monoclonal antibody drug to CD20 in overseas, and also has begun to be used for intractable vasculitis (see non-patent document 2). These antibody drug in which the antigens are identified are not specific to the intractable vasculitis, and it is considered that the antigen is neutralized by direct reactions with the antibodies. Antibody medicines currently used are always associated with risks because these antibody drugs were not developed against an antigen specific for an intractable vasculitis.

Administration of large amounts of immunoglobulins is effective for treatment of intractable vasculitis. In detail, the diversity of immunoglobulins consists of $10^8$ clones. Their molecular structure comprises light chains (L chains) and heavy chains (H chains), in which two kinds of polypeptides are linked by disulfide bonds. The heavy chain comprises a constant region (C region) and a variable region (V region) composed of a VH region. On the other hand, the light chain includes a constant region consisting of a CL region, and a variable region consisting of a VL region is connected. Various antibodies to diverse antigens are made in vivo due to diversity of the amino acid sequence of the variable region.

There are several hypotheses for the mode of action of immunoglobulin drugs. The first hypothesis is that many kinds of antibodies against unknown antigens exhibit a pharmacological effect. The second hypothesis is also that antibodies against an auto-antibody myeloperoxidase (MPO) against to MPO (anti-MPO antibody) are effective (non-patent literature 3). In particular, a variety of anti-MPO antibodies against a wide variety of epitopes of MPO exhibit pharmacological effects. Similarly, an antibody against anti-moesin antibody, which is a self-antibody that is involved in the severity of intractable vasculitis antibody is effective (patent reference-1 and non-patent references 4-5). In common between both hypotheses, the immunoglobulin medicine is a mixture of a lot of varieties of immunoglobulins, that is, polyclonal antibodies contribute to a therapeutic effect. Another hypothesis is that a variety of antibodies against a specific antigens exhibit efficacy.

It is known that a single clone ScFv of a human recombinant antibody exhibits a therapeutic effect to an intractable vasculitis model mouse (patent reference 2-5). Under this situation, it is required to develop recombinant antibody drug for an intractable vasculitis using the antibody targeted by the specific antigen for reduction of infection risk of the patients and to elucidate its mechanisms of a recombinant immunoglobulin.

If the antigen of antibody is specified, the antibody drug can be produced by recombinant DNA technology using the recombinant ScFv as a model. The chimeric antibody and humanized antibody have already been practically used as antibody drugs (patent references 6-7). It is known that immunoglobulin protein fused with chaperon is produced as a technique of production of soluble normal proteins by expression of immunoglobulin genes in host cells. All of these are a single molecule immunoglobulin, that is, a monoclonal immunoglobulin or its fragment.

CITATION LIST

Patent Documents

Patent document 1: International publication no.
Patent document 2: US patent application ser/0164290
Patent document 3: JP-A 2013-147495
Patent document 4: US patent application publication no. 2015/0166645
Patent document 5: Japanese patent application laid-open no. 2016-16628
Patent document 6: Japanese patent application laid-open no. 5-304989
Patent document 7: Japanese patent application laid-open no. 2000-14383
Patent document 8: Japanese patent application laid-open no. 2004-89199

Non-Patent Document

Non-patent document 1: Gilberto Poggioli, Silvio Laureti, Massimo Campieri, Filippo Pierangeli, Paolo Gionchetti, Federica Ugolini, Lorenzo Gentilini, Piero Bazzi, Fernando Rizzello, and Maurizio Coscia. Infliximab in the treatment of Crohn's disease. Ther Clin Risk Manag. 2007 Jun.; 3(2): 301-308.

Non-patent document 2: Watts R A, Scott D G. Vasculitis and inflammatory arthritis. Best Pract Res Clin Rheumatol. 2016 Oct.;30(5):916-931.

Non-patent document 3: Goeken J A. Antineutrophil cytoplasmic antibody-A useful serological marker for vasculitis. J Clin Immunol 1991; 11: 161-174

Non-patent document 4: Suzuki K, Nagao T, Itabashi M, Hamano Y, Sugamata R, Yamazaki Y, Yumura W, Tsukita S, Wang P C, Nakayama T, Suzuki K. A novel autoantibody against moesin in the serum of patients with MPO-ANCA-associated vasculitis. Nephrol Dial Transplant. 2014 Jun.; 29(6):1168-77.

Non-patent document 5: Ellen F. Carney. VASCULITIS: Potential role of an antimoesin autoantibody in AAV Nature Reviews Nephrology 2014; 10:3.

Non-patent document 6: Ito-Ihara T, Ono T, Nogaki F, Suyama K, Tanaka M, Yonemoto S, Fukatsu A, Kita T, Suzuki K, E. Muso. Clinical efficacy of intravenous immunoglobulin for patients with MPO-ANCA-associated rapidly progressive glomerulonephritis. Nephron Clin Pract. 2005; 102:c35-c42.

Non-patent document 7: Unizony S, Villarreal M, Miloslaysky E M, Lu N, Merkel P A, Spiera R, Seo P, Langford C A, Hoffman G S, Kallenberg C M, St Clair E W, Ikle D, Tchao N K, Ding L, Brunetta P, Choi H K, Monach P A, Fervenza F, Stone J H, Specks U; RAVE-ITN Research Group. Clinical outcomes of treatment of anti-neutrophil cytoplasmic antibody (ANCA)-associated vasculitis based on ANCA type. Ann Rheum Dis. 2015 Nov. 30. pii: annrheumdis-2015-208073. doi: 10.1136/annrheumdis-2015-208073. [Epub ahead of print]

Non-patent document 8: de Joode A A, Roozendaal C, van der Leij M J, Bungener L B, Sanders J S, Stegeman C A. Performance of two strategies for urgent ANCA and anti-GBM analysis in vasculitis. Eur J Intern Med. 2014 Feb.; 25(2):182-6. doi: 10.1016/j.ejim.2013.11.011. Epub 2013 Dec. 19.

Non-patent document 9: Kallenberg C G, Stegeman C A, Heeringa P. Autoantibodies vex the vasculature. Nat. Med. 2008 Oct.;14(10):1018-9.

Non-patent document 10: Kain R, Exner M, Brandes R, Ziebermayr R, Cunningham D, Alderson C A, Davidovits A, Raab I, Jahn R, Ashour O, Spitzauer S, Sunder-Plassmann G, Fukuda M, Klemm P, Rees A J, Kerjaschki D. Molecular mimicry in pauci-immune focal necrotizing glomerulonephritis. Nat. Med. 2008 Oct.;14(10):1088-96. Epub 2008 Oct. 5.

Non-patent document 11: Tomizawa K, Nagao T, Kusunoki R, Saiga K, Oshima M, Kobayashi K, Nakayama T, Tanokura M, Suzuki K. Reduction of MPO-ANCA epitopes in SCG/Kj mice by 15-Deoxyspergualin treatment restricted by IgG2b associated with crescentic glomerulonephritis. Rheumatology (Oxford). 2010;49:1245-56.

SUMMARY OF INVENTION

Technical Problem

As described above, there is currently no standard therapy for intractable vasculitis. Treatment methods using antibody drugs have also been studied, but they are not developed for a therapeutic drug specialized for intractable vasculitis. This means that no standard therapeutic drug for intractable vasculitis has been present whereas only use of steroids is described in a guideline for the disease nowadays.

The present invention provides a therapeutic method specialized for inflammatory diseases such as intractable vasculitis and infectious diseases according to determination of target molecules of these diseases which is different therapeutic methods from the prior to the method with unknown target molecules.

Technical Solution

The present inventors have intensively studied to solve the above-described problems. As a results of overcoming much difficulties in the process, the present inventors determined that the target antigen of the clone ("VasSF"), which shows various therapeutic effects of a human single-chain variable fragment (hScFv) on a mouse model of intractable vasculitis (patent document 5) as in Sequence No. 31 comprising an amino acid sequence represented, was apolipoprotein A2 (APOA2). As these results, the present inventors the present invention has been completed as resent invention has been completed. As a result, the present inventors have found that use of an antibody that specifically recognizes APOA2 makes it possible to prevent and/or treat inflammatory diseases such as vasculitis and infectious diseases, and completed the present invention.

In other words, according to one form of the present invention, a prophylactic and/or therapeutic agent, which contains an antibody recognizing apolipoprotein A2 (APOA2) as a specific antigen, is provided for infectious diseases and inflammatory.

According to another aspect of the invention, recombinant fragments of immunoglobulins of anti-APOA2 (SEQ ID NO: 4) and polypeptides of immunoglobulins of anti-APOA2 containing the same or substantially the same amino acid sequences as the amino acid sequence represented by the expression (SEQ ID NO: 4) are provided.

According to further aspect of the invention, a vector containing polynucleotide encoding a polypeptide containing the same or substantially identical amino acid sequence as the amino acid sequence represented by the structure containing the polynucleotide and its polynucleotide, and a host cells containing its vector (SEQ ID NO: 4) are provided.

According to further aspect of the invention, methods including administration of an effective amount of anti-APOA2 antibody for preventing and/or treating infectious diseases or inflammatory diseases, and methods for screening a prophylactic and/or therapeutic agent for infectious diseases or inflammatory diseases using apolipoprotein A2 (APOA2) are provided.

According to yet another aspect of the present invention, induction reagents containing an apolipoprotein A2 (APOA2) for infectious diseases or inflammatory diseases as an effective component, procedures for preparation of a model mouse of infectious diseases or inflammatory diseases by administration of apolipoprotein A2 (APOA2) into a non-transgenic animal except humans, and the pathological model animal of the infectious diseases or inflammatory diseases induced with this procedures are provided.

Technical Effect

In the process of completing the present invention, the target molecule for the effective on treating inflammatory diseases or infectious diseases such as an intractable vasculitis was identified. Based on the evidence, it is possible that a specific treatment method is provided which is different from the previous methods.

DESCRIPTION OF EMBODIMENTS

Figure 1A:
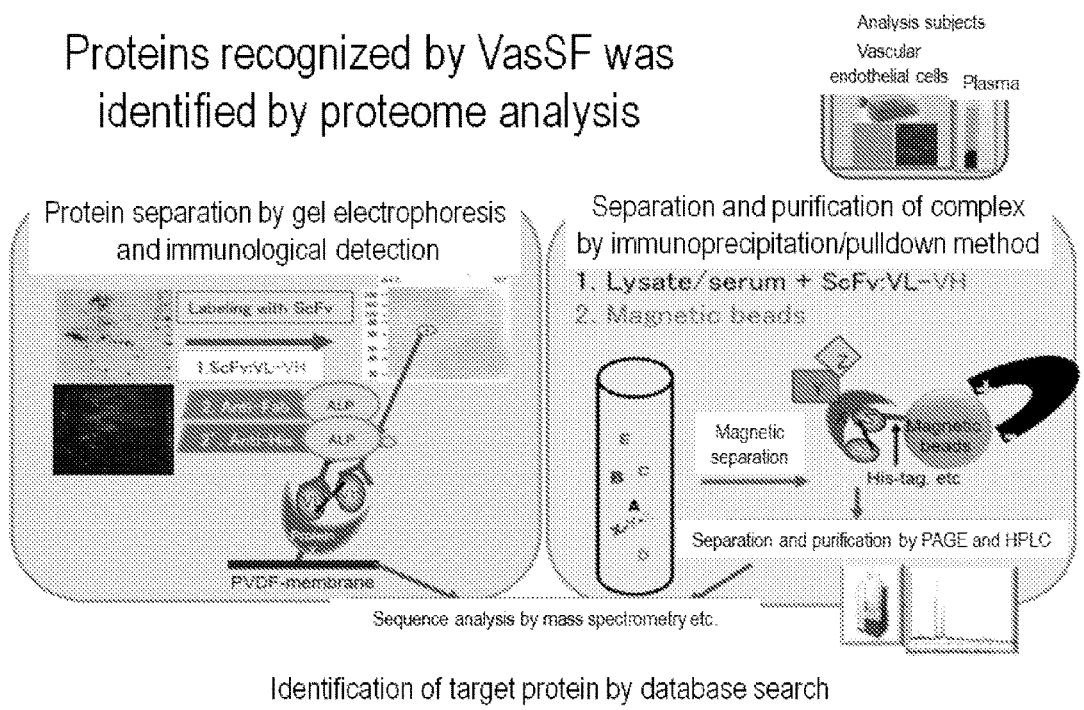
FIG. 1A Illustration describing a method used for identification of an antigen targeted by a specific antibody.

The first embodiment of the present invention is a prophylactic and/or therapeutic agent for infectious diseases or inflammatory diseases relates to apolipoprotein A2 (APOA2) as an active ingredient.

The present inventors have outlined how the present inventors have completed the present invention, first, the inventors of the present invention (5) showing various therapeutic effects on the intractable vasculitis model mice: The present inventors have been screening a target molecule by a human single-chain variable fragment (hscFv) comprising an amino acid sequence represented by the following formula (31)=hScFv clone which is also referred to as "VasSF"). However, the discovery of antigens was very difficult, even if a variety of methods were tried as described in the column of the embodiment later, the antigen could not be easily identified. Finally, the present inventors identified the target antigen of VasSF, thereby completed the present invention.

That is, the present inventors surprisingly identified that the target antigen of VasSF is apolipoprotein A2 (APOA2) which is a protein: it has not been completely known in association with infectious diseases and inflammatory diseases. Using this antibody that specifically recognizes APOA2, it is possible to prevent and/or treat inflammatory diseases such as intractable vasculitis and infectious diseases. The human apolipoprotein A2 (hPOA2) is encoded in 473-bp-long APOA2 gene (RefSeq accession no. NM 001643; CDS sequence corresponds to SEQ ID NO:1) and comprises 100 amino acids (RefSeq accession No. NP 001634, SEQ ID NO: 2).

Based on the several findings described above, the present inventors have completed the present invention. Hereinafter, the present invention will be described in detail, the technical scope of the present invention is not limited to the following modes.

Protein (Antigen)

Apolipoprotein A2 (APOA2) used in the present invention; "the protein of the present invention is also referred to as "protein of the present invention") is a protein having the same sequence of amino acids or substantially the same sequence by the formula 2. The proteins of the present invention include humans and other warm-blooded animals (for example, guinea pigs, rats, mice, chicken, rabbits, pigs, sheep, bovine, monkey, and the like) of cells (e.g., hepatocytes, spleen cells, and nerve cells), glial cells, pancreatic beta cells, bone marrow cells, mesangial cells, Langerhans cells, and epidermal cells, epithelial cells, goblet cells, endothelial cells, smooth muscle cells, and fibroblast cells, muscle cells, adipocytes, immune cells (e.g., macrophages, T cells, and B cells, natural killer cells, mast cells, neutrophils, basophils, eosinophils, monocytes), megakaryocytes, synovial cells, chondrocytes, osteocytes, osteoblasts, osteoclasts, mammary gland cells or stromal cells, or progenitor cells of these cells, stem cells or cancer cells) or any tissue in which these cells exist (e.g., the brain, the hippocampus, the thalamus, the hypothalamus, the cerebral cortex, the medullary canal, the cerebellum, the spinal cord, and the pituitary, stomach, pancreas, kidney, liver, gonads, thyroid, gallbladder, bone marrow, adrenal, and skin, muscle (e.g., smooth muscle, skeletal muscle), lung, digestive tract (e.g., colon, small intestine)), the blood vessel, the heart, the thymus, the spleen, and the submandibular gland, peripheral blood, prostate, testis, ovary, placenta, uterus, bone, joint, adipose tissue (e.g., white adipose tissue, brown adipose tissue) and the like. The protein may be a purified protein from above source. Alternatively, the protein may be a protein which is chemically synthesized by a chemical synthesis or a cell-free translation system, or a recombinant protein produced from a transformant in which a nucleic acid having a nucleotide sequence encoding the amino acid sequence is introduced.

The amino acid sequence substantially identical to the amino acid sequence represented by SEQ ID NO 2 is the amino acid sequence represented by the formula about 50% or more, and preferably about 60% or more, more preferably about 70% or more, even more preferably about 80% or more, and particularly preferably about 90% or more, and most preferably, an amino acid sequence having homology (homology) of about 95% or more in the SEQ ID NO 2. Here, "homology" means and the ratio (%) of the overlapping residues of the same amino acid and similar amino acid in total amino acids which are referred to a mathematical algorithm known in the art when one of the amino acid sequence is aligned with another amino acid sequence (the algorithm may take into account the introduction of a gap into one or both of the sequences for optimal alignment). "Similar amino acid" refers to amino acids similar in physicochemical properties, for example, an aromatic amino acid (Phe, Trp, Tyr), aliphatic amino acids (Ala, Leu, Ile, Val), polar amino acids (Gln, Asn); basic amino acids (Lys, Arg, His), acidic amino acids (Glu, Asp), an amino acid having a hydroxyl group (Ser, Thr), and an amino acid having a small side chain (Gly, Ala, Ser, Thr, Met). Substitution with similar amino acids does not result in changes in the phenotype of the protein (that is, conservative amino acid substitutions). Specific examples of conservative amino acid substitutions are well known in the art and are described in various references (see, for example, Bowie et al. Science, 247: 1306-1310 (1990)).

Homologies of amino acid sequences in this specification were calculated with homology calculation algorithm of NCBI BLAST (National Center for Biotechnology Information Basic Local Alignment Search tool) under the following conditions (expected value=10; gap are permitted; matrix=BLOSUM62; filtering=OFF). Other algorithms for determining homology of amino acid sequences, for example, Karlin et al., Proc Natl Acad Sci USA, 90: 5873-577 (1993)) [the algorithm is incorporated into the NBLAST and XBLAST program (version 2.0) (Altschul et al. Nucleic Acids Res, 25: 3389-3402 (1997))], Needleman et al., J Mol. Biol, (48): 444-453 (1970) [The algorithm is incorporated into the GAP program in the GCG software package], Myers and Miller, CABIOS, 4: 11-17 (1988) [the algorithm is incorporated into the ALIGN program (version 2.0) in a CGC sequence alignment software package; and Pearson et al., Proc Natl Acad Sci USA, 85: 2444-2448 (1988) [the algorithm is incorporated into the FASTA program in a GCG software package] are also preferably used.

More preferably, the amino acid sequence having substantially the same amino acid sequence as the amino acid sequence represented by SEQ ID NO: (2) is the amino acid sequence with about 50% or more, and preferably about 60% or more, more preferably about 70% or more, even more preferably about 80% or more, and particularly preferably about 90% or more, most preferably at least about 95% identity.

The protein used in the present invention is a protein with substantially the same amino acid sequence as represented by SEQ ID NO: (2), and with substantially identical activities as those of a protein containing the amino acid sequence represented by SEQ ID NO: (2).

The substantially identical activities include, for example, ligand binding activity and signal transduction. Here, "substantially identical" means qualitatively (e.g., physiologically or pharmacologically) identical. Thus, it is preferable that the protein of the present invention has the identical activity. However, the degree of the activity (e.g., about 0.01 to about 100 times, preferably from about 0.1 to about 10 times, more preferably from 0.5 to 2 times) or a quantitative element such as a molecular weight of the protein may be different.

Measurement of activities, such as ligand binding and signal transduction, can be carried out in accordance with known methods. For example, the activities can be measured by a method used in the screening method, and the like, for compounds or their salts, which inhibit the activity of a protein used in the present invention, which will be described later.

The proteins used in the present invention include proteins with, for example, (i) one or more amino acid residues (for example, from one to 50, and preferably from one to 30, more preferably from one to 10, and even more preferably from one to five, four, three, or two amino acid residues) are deleted from the amino acid sequence represented by SEQ ID NO: 2, (ii) one or more amino acid residues (for example, from one to 50, and preferably from one to 30, more preferably from one to 10, and even more preferably from one to five, four, three, or two amino acid residues) are added to the amino acid sequence represented by SEQ ID NO: 2, (iii) one or more amino acid residues (for example, from one to 50, and preferably from one to 30, more preferably from one to 10, and even more preferably from one to five, four, three, or two amino acid residues) are inserted into the amino acid sequence represented by SEQ ID NO: 2, (iv) one or more amino acid residues (for example, from one to 50, and preferably from one to 30, more preferably from one to 10, and even more preferably from one to five, four, three, or two amino acid residues) are substituted to different amino acid residues from the amino acid sequence represented by SEQ ID NO: 2, and (v) modifications combined above of amino acid sequence, so-called mutein.

When the amino acid sequence is inserted, deleted or substituted as described above, the positions of insertion, deletion, or substitution are not specifically limited.

Preferred examples of proteins used in the present invention include, for example, human apolipoprotein A2 (RefSeq Accession No. NP_001634) containing the amino acid sequence shown in SEQ ID NO: (2), and it's homologs in another mammals.

In this specification, the protein and peptide are depicted in accordance with the convention of the peptide with N-terminals (amino terminals) and C-terminals (carboxyl terminals) at the left and right ends, respectively. Proteins used in the present invention including a protein containing an amino acid sequence represented by SEQ ID NO: 2 may have a carboxyl group (—COOH), a carboxylate (—COO⁻), an amide (—CONH$_2$) or an ester (—COOR) at the C-terminal.

Furthermore, proteins used in the present invention contain proteins with an amino group of the amino acid residue at N-terminal (e.g., methionine residue)) of which are protected by protecting groups (for example, formyl group, C1-6 acyl groups such as C1-6 alkanoyl such as acetyl group), proteins with glutamine residues produced by in vivo cleavage and pyroglutamated, proteins of which substituent groups (e.g., —OH, —SH, amino groups, imidazole groups, indole groups, and guanidine groups) in intramolecular side chains of amino acid resides are protected by appropriate protecting groups (for example, formyl group, C$_{1-6}$ acyl groups such as C$_{1-6}$ alkanoyl such as acetyl group), complex proteins such as so-called glycoproteins with glycosylation.

The partial peptides of the protein used in the present invention may be any peptides as long as they have partial amino acid sequence of the protein used in the present invention described above and also have substantially identical activity as that of the protein. Here, "substantially identical activity" is defined the same as that described above. The "substantially identical activity" can be measured in the same manner for the protein in the present invention as described above.

For example, peptides containing at least 20-amino-acid-long or longer, preferably 50- or longer, more preferably 70- or longer, more preferably 100- or longer, and most preferably 150- or longer of the constituent amino acid sequence of the protein used in the present invention can be used.

The partial peptides used in the present invention can be used even though one amino acid or more (preferably one to 20, more preferably one to 10, more preferably several (one to five, four, three or two) are deleted, one amino acid or more (preferably one to 20, more preferably one to 10, more preferably several (one to five, four, three or two) are added, one amino acid or more (preferably one to 20, more preferably one to 10, more preferably several (one to five, four, three or two) are inserted, or one amino acid or more (preferably one to 20, more preferably one to 10, more preferably several (one to five, four, three or two) are substituted to different amino acids in their amino acid sequences.

The partial peptides used in the present invention can also be used as antigens for antibody preparation. Proteins or its partial peptides used in the present invention may be in free or salt forms (hereinafter, the same unless otherwise specified). Such salts include physiologically acceptable acids (e.g., inorganic acids, and organic acids) and salts with bases (e.g., alkali metal salts). In particular, physiologically acceptable acid addition salts are preferred. Examples of such salts include inorganic acids (e.g., hydrochloric acid, phosphoric acid, hydrobromic acid, and sulfuric acid) and organic acids (e.g., acetic acid, formic acid, propionic acid, fumaric acid, maleic acid, succinic acid, tartaric acid, citric acid, malic acid, oxalic acid, benzoic acid, methanesulfonic acid, and benzenesulfonic acid).

The proteins used in the present invention can be derived from cells or tissues of humans or other warm-blooded animals mentioned above by purification using known protein purification methods. Specifically, for example, proteins used in the present invention can be prepared by homogenization of tissues or cells of mammals in the presence of detergents and purification from the crude extract fraction by chromatography, such as reverse phase chromatography, ion exchange chromatography, and affinity chromatography.

The proteins or their partial peptides used in the present invention can also be produced according to known peptide synthesis methods.

Partial peptides of the proteins used in the present invention can be produced by fragmentation of proteins used in the present invention with suitable peptidases.

Furthermore, the proteins or their partial peptides used in the present invention can be produced by separation and purification of the proteins or their partial peptides from culture products of transformants containing polynucleotides encoding the proteins or their partial peptides.

Antibodies of the Present Invention

Antibodies against proteins or their partial peptides used in the present invention (hereinafter also referred to as "antibodies of the present invention") can be either polyclonal or monoclonal antibodies if they specifically recognize the proteins or their partial peptides. The isotypes of the antibodies are not particularly limited, but preferably IgG, IgM or IgA, and particularly preferably IgG.

The antibodies of the present invention are not particularly limited if at least they have complementarity determining regions (CDR) for specific recognition and binding to their targets. The antibodies of the present invention may be complete molecules of the antibodies and their fragments such as Fab, Fab', F(ab'), ScFv, ScFv-Fc, genetically-engineered conjugate molecules such as mini-bodies and diabodies, or derivatives modified with molecules having protein stabilizing actions such as polyethylene glycol (PEG).

The antibodies of the present invention include, for example, polypeptides containing the same or substantially identical amino acid sequence shown in SEQ ID NO: 4 (preferably, polypeptides with the same or essentially the same amino acid sequence represented in SEQ ID NO: 4). In other words, according to another embodiment of the present invention, anti-APOA2 recombinant immunoglobulin fragment compounds containing polypeptides containing the same or essentially the same amino acid sequence represented in SEQ ID NO 4 (preferably, polypeptides with the same or essentially the same amino acid sequence represented in SEQ ID NO 4) as active ingredients are provided. These anti-APOA2 recombinant immunoglobulin fragment compounds are preferably used for the prevention and/or treatment of infectious diseases or inflammatory diseases.

Antibodies to the proteins or their partial peptides used in the present invention (hereinafter they are also referred to simply as "proteins of the present invention" in the description of antibodies) can be produced according to known methods for antibody or anti-serum production.

The method for preparation of antigens for antibodies in the present invention and method for production of the antibodies are described below.

Either proteins or partial peptides in the present invention described above, or (synthetic) peptides containing one, two, or more of the same antigenic determinants thereof (hereinafter these are also referred to simply as "antigens of the present invention") may be used as antigens for preparation of antibodies of the present invention.

Proteins or their partial peptides of the present invention is produced by, for example, (a) known or similar preparation methods with tissues or cells of warm-blooded animals such as humans, monkeys, rats, mice, and chicken, (b) known chemical preparation methods with peptide synthesizers or similar machines, (c) culture of transformants containing DNA encoding the proteins or their partial peptides in the present invention, or (d) biochemical synthesis using cell-free translation/transcription with DNA encoding the proteins or their partial peptides in the present invention as templates.

(a) Preparation of Cells Producing Monoclonal Antibodies

Antigens of the present invention, alone, or accompanied with carriers and/or diluents, are administered to warm-blooded animals at sites capable of antibody production by, e.g., intraperitoneal, intravenous, subcutaneous, or intradermal injections. To enhance antibody production ability upon administration, complete or incomplete Freund's adjuvants may be administered. Administrations are usually performed once every one to six weeks, twice to 10 times in total. The warm-blooded animals used for antibody production include, for example, monkeys, rabbits, dogs, guinea pigs, mice, rats, hamsters, sheep, goats, donkeys, and a chicken. To avoid the problem of anti-Ig antibody production, it is preferable to use the same kind of mammals as the subjects to be administered. However, mice and rats are preferably used for monoclonal antibody productions.

The artificial immunization for humans is ethically difficult. Therefore, when the antibody of the present invention is to be administered to humans, following methods are preferable for production of human antibodies: (i) immunization of human-antibody-producing animals (for example, a mice) prepared according to a method described later, (ii) preparation of humanized antibodies or complete human antibodies in accordance with a method for production of chimera antibodies described later, or (iii) combinations of in vitro immunizations, virus-based cell immortalizations, human-human (or mouse) hybridoma production techniques, phage display method, etc. In vitro immunization methods are also preferably used because antibodies may be produced against antigens which suppress antibody productions in regular in vivo immunization, antibodies can be obtained with only a little amount (ng to pg order) of antigens, and immunization can be completed in several days.

Animal cells used for in vitro immunization methods include lymphocytes, preferably B lymphocytes from peripheral blood, spleens, lymph nodes, etc., of humans and warm-blooded animals described above (preferably mice and rats). For example, in case of mouse and rat cells, the spleen is excised from animals of 4 to 12 weeks of age and then spleen cells are isolated. The spleen cells are washed in a suitable medium (e.g., Dulbecco's modified eagle's medium (DMEM), RPMI 1640 medium, Ham's F12 medium) and then cultured in a medium with antigens and 5 to 20% of fetal bovine serum (FCS) in a $CO_2$ incubator for to 10 days. The antigen concentration at 0.05 to 5 µg is recommended, but not limited. Addition of supernatants from cultures of splenocytes from the same strain of animals (1 to 2 weeks of age is preferable) prepared in accordance with a conventional method to the culture medium is preferable.

For in vitro immunization of human cells, cytokines such as IL-2, IL-4, IL-5, IL-6, and optionally adjuvant substances (e.g., Muramyl dipeptide) should be added to the medium together with the antigens because it is difficult to obtain supernatants from cultures of human thymus cells.

(b) Purification of Monoclonal Antibodies

Separation and purification of monoclonal antibodies can be performed by known methods, for example, immunoglobulin separation and purification methods [e.g., salting-out methods, alcohol sedimentation methods, isoelectric point precipitation methods, electrophoretic methods, ion exchanger (e.g., DEAE, and QEAE) adsorption/desorption methods, ultracentrifuge methods, gel filtration methods, or specific purification methods for obtaining antibodies by elution after specific binding of antibodies to active adsorbents such as carriers bound to antigens, protein A or protein G).

As described above, after cultures of the hybridoma in vivo in warm-blooded animals or in vitro, monoclonal antibodies can be produced by collecting the antibodies from the body fluid or culture fluid.

Since the antibodies in the present invention must have a therapeutic activity against infectious diseases and inflammatory diseases when the antibodies are used for prevention and treatment of these diseases, it is necessary to examine the level of the therapeutic activity of the obtained monoclonal antibodies. The therapeutic activity can be measured by comparison of efficacies between disease model animals treated with and without the antibodies.

In preferred embodiments, the antibodies of the present invention are used as a medicine to be administered to humans. Therefore, antibodies (preferably monoclonal antibodies) of the present invention have a reduced risk to induce antigenicity when administered to humans (specifically, complete human antibodies, humanized antibodies, mouse-human chimeric antibodies, etc.), and particularly preferably complete human antibodies. The humanized antibodies and the chimeric antibodies can be genetically engineered according to a method described below. In addition, as described above, the complete human antibodies can be produced from the human-human (or mouse) hybridomas, but the methods with human antibody-producing animals (for example, mice) or phage display methods described later are preferable for stable and inexpensive production of a large amount of antibodies.

(i) Preparation of Chimeric Antibodies

In this specification, "chimeric antibodies" refers to antibodies of which variable regions of H and L chains ($V_H$ and $V_L$) are derived from one mammalian species and constant regions ($C_H$ and $C_L$) are derived from another mammalian species. Amino acid sequences of variable regions are preferably derived from animal species which can be used for easy production of hybridomas, such as mice. On the other hand, sequences of the constant regions are preferably derived from a mammalian species to be administered.

Methods for preparation of chimeric antibodies in the present invention are, for example, the method of U.S. Pat. No. 6,331,415, or partially modified methods. Fab and F(ab')$_2$ can be prepared by papain and pepsin digestions, respectively, of obtained chimeric antibodies.

In addition, the ScFv can be made by combining DNA encoding mouse $V_H$ and $V_L$ regions with suitable linkers encoding, for example, one to 40 amino acids, preferably three to 30 amino acids, more preferably five to 20 amino acids (e.g., [Ser-(Gly)$_m$]$_n$ or [(Gly)$_m$-ser]$_n$ (m is an integer of Zero to 10, n is an integer of one to five) or the like). Furthermore, minibody monomers can made by combining ScFv with DNA encoding CH3 via suitable likers. ScFv-Fc can be made by combining ScFv with DNA encoding full sequence of $C_{H3}$ via suitable likers. DNAs encoding such genetically modified (conjugated) antibody molecules can be expressed in *E. coli* or yeasts when the DNAs are placed under the control of an appropriate promoter and a large amount of antibody molecules can be produced.

When DNAs encoding mouse VH and VL are inserted in tandem in the downstream of one promoter and then introduced into *E. coli*, dimers called Fv are produced by monocistronic gene expression. When suitable amino acids in the FR of VH and VL are replaced with Cys using molecular modeling, dimers called dsFv are formed by intermolecular disulfide bonds between both chains.

(ii) Humanized Antibodies

In this specification, "humanized antibodies" refer to antibodies in which sequences other than the complementarity determining regions (CDR) in variable regions (i.e., constant regions and framework regions (FR) of variable regions) are derived from humans and only the CDR sequences are derived from other mammalian species. As the "other mammalian species", animal species which can be used for easy production of hybridomas, such as mice, are preferable.

As methods for producing humanized antibodies, for example, ones in U.S. Pat. Nos. 5,225,539, 5,585,089, and 5,693,761, and methods described in U.S. Pat. No. 5,693,762, or partially modified methods can be used. Humanized antibodies can also be converted into ScFv, ScFv-Fc, minibody, dsFV, Fv or the like by genetic engineering techniques as well as chimeric antibodies. The antibodies can be produced by a suitable promoter in microorganisms such as *E. coli* and yeasts.

Techniques for producing humanized antibodies, for example, can be applied to produce monoclonal antibodies in animals in which hybridoma production is not established and the produced antibodies can be preferably administered to the animal species. For example, widely propagated livestock (poultry) such as bovine, porcine, sheep, goats, chicken and the like, and pet animals such as dogs and cats can be targets of therapy with humanized antibodies.

(iii) Preparation of Complete Human Antibodies Using Human Antibody-Producing Animals When functional human immunoglobulin (Ig) genes are introduced into non-human warm-blooded animals with knockout (KO) of endogenous Ig genes and then the animals are immunized with antigens, human antibodies are produced in place of antibodies derived from the animals. Thus, by using animals in which hybridoma production techniques have been established, such as mice, complete human monoclonal antibodies can be obtained by a method similar to that of the conventional mouse monoclonal antibody production.

When the antibodies of the present invention are used as pharmaceutical agents, they are preferably monoclonal antibodies, but polyclonal antibodies are also acceptable. When the antibodies of the present invention are polyclonal antibodies, the use of hybridomas is not required. Therefore, the animals in which the hybridoma production technique is not established but the transgenic technique is established, preferably ungulates like bovine, can be used for a larger amount of human antibodies at a low cost with similar methods described above (See, for example, Nat. Biotechnol., 20: 889-994 (2002)). The resulting human polyclonal antibodies can be obtained by purification from blood, ascites, milk, eggs, etc., preferably from milk or eggs, of human antibody-producing animals by the combination of the same purification techniques as described above.

(iv) Preparation of Complete Human Antibodies Using Phage Display Human Antibody Libraries Another approach for producing complete human antibodies is a method using phage display. In this method, mutation by PCR errors may be introduced to sites other than CDR, and, as a result, there is a small number of reports of HAHA production in a clinical stage. On the other hand, the method has some advantages that there is no risk of xenogenic viral infection from host animals, and that the infinite specificity of the antibodies can be expected (antibodies against prohibited clones and sugar chains, etc., can be easily prepared). The method for preparing the phage display human antibody libraries is not particularly limited.

(3) Preparation of Polyclonal Antibodies

The polyclonal antibodies of the present invention can be produced in accordance with known or similar methods. For example, using immunogens (protein or peptide antigens) alone or complexes of immunogens and carrier proteins, the warm-blooded animals are immunized in the same manner as in the production method of the monoclonal antibodies. Then, antibodies against the proteins in the present invention can be produced by the collection of antibody-containing substances from the immunized animals and separation/purification of the antibodies.

Polyclonal antibodies are collected from, e.g., blood, and ascites (preferably blood) of warm-blooded animals immunized in the manner described above.

Polyclonal antibody titers in antisera can be measured in the same manner as the measurement of the monoclonal antibody titers in the antiserum as described above. Polyclonal antibodies can be separated and purified by the method similar to ones for the separation/purification of monoclonal antibodies as described above.

The protein of the present invention or partial peptides thereof (hereinafter, simply referred to as "protein of the present invention"), a DNA encoding the protein of the present invention or partial peptides thereof, and applications of the antibodies of the present invention are described below.

Since the protein is a target molecule of the antibodies of the present invention, the presence, absence, or degree of expression of the protein of the present invention in patients affected or suspected to be affected by infectious diseases or inflammatory diseases can be used as an index for the estimation of efficacies of the antibodies of the present invention for the prevention/treatment to the diseases.

By the inhibition of the activity of the protein (APOA2) of the present invention, infectious diseases or inflammatory diseases can be prevented or treated. Therefore, the antibodies of the present invention can be used as medicines for prevention/treatment of infectious diseases or inflammatory diseases. From other viewpoints, the present invention includes methods for preventing and/or treating infectious diseases or inflammatory diseases by administering an effective amount of the antibodies of the present invention. In this case, persons like medical doctors can appropriately determine effective amount by, e.g., the degree of activity of the antibodies, the physical conditions of the patient, the conditions of the disease. Infectious diseases are broadly interpreted and cover a wide variety of infections of foreign agents (for example, infection of various bacteria, viruses, or parasites, and sepsis caused by these pathogens). The inflammatory diseases include intractable vasculitis (for example, idiopathic thrombocytopenic purpura, agammaglobulinemia, Kawasaki disease, Guillain-Barre syndrome, Microscopic PolyAngitis (MPA), and Eosinophilic granulomatosis with polyangiitis (e.g., PA, Churg-Strauss syndrome)), nephritis and/or glomerulonephritis, idiopathic pulmonary fibrosis, etc.

Medicines containing the antibodies of the present invention for prevention/treatment of disease has a low toxicity, and can be administered as liquid medicine or medicine in an appropriate dosage forms to human or mammals (e.g., rats, rabbits, sheep, porcine, bovine, cats, dogs, and monkeys) orally or parenterally like intravascularly, subcutaneously, and intramuscularly.

The antibodies of the present invention may be administered alone, or may be administered as a suitable pharmaceutical composition. The pharmaceutical composition used for administration may contain the antibodies of the present invention and a salt thereof and a pharmacologically acceptable carriers, diluents or excipients. Such pharmaceutical compositions are provided as dosage forms suitable for oral or parenteral administration.

As compositions for parenteral administration, for example, injections, suppositories, etc. are used, and dosage forms for injections may include intravenous, subcutaneous, intradermal, intramuscular, drip injections and the like. Such injections can be prepared according to known methods. The injection can be prepared, for example, by dissolving, suspending or emulsifying the above-mentioned antibodies of the present invention or a salt thereof in a sterile aqueous or oil solutions usually used for injection. As the aqueous solution for injection, for example, physiological saline, isotonic solution containing glucose and other adjuvants, etc. are used, and suitable solubilizers such as alcohol (e.g., ethanol), polyalcohol (e.g., propylene glycol, polyethylene glycol), nonionic surfactants (e.g., polysorbate 80, HCO-50 (polyoxyethylene (50 mol) adduct of hydrogenated castor oil)) and the like. As an oily liquid, for example, sesame oil, soybean oil and the like are used, and benzyl benzoate, benzyl alcohol and the like may be used in combination as a solubilizing agent. The prepared injection solution is preferably filled in suitable ampoules. Suppositories to be used for rectal administration may be prepared by mixing the above-mentioned antibodies or a salt thereof with a conventional suppository base.

Compositions for oral administration may be in solid or liquid dosage forms, specifically tablets (including coated tablets, film coated tablets), pills, granules, powders, capsules (including soft capsules), syrups, emulsions, suspensions and the like. Such compositions are prepared by known methods, and may contain carriers, diluents or excipients commonly used in the field of formulation. As a carrier or excipient for tablets, for example, lactose, starch, sucrose and magnesium stearate are used.

The above-mentioned parenteral or oral pharmaceutical compositions are conveniently prepared in dosage unit form adapted to the dose of the active ingredient. Such dosage unit forms include, for example, tablets, pills, capsules, injections (ampules), suppositories. The content of the antibodies is preferably 5 to 500 mg per dose unit dosage form, particularly 5 to 100 mg for an injection, and 10 to 250 mg for the other dosage form.

Although the dose of the above-mentioned preparation containing the antibodies of the present invention varies depending on the administration subject, target disease, condition, administration route etc., for example, when used for treatment/prevention of an adult, the dosage of the antibodies of the present invention is usually about 0.01 to 20 mg/kg body weight, preferably about 0.1 to 10 mg/kg body weight, more preferably about 0.1 to 5 mg/kg body weight, about 1 to 5 times a day, preferably 1 to 3 times a day, and is preferably administered by intravenous injection. In the case of other parenteral administration and oral administration, similar amounts can be administered. If the condition is particularly severe, the dose may be increased according to the condition.

Each composition described above may contain other active ingredients as long as the formulation with the above antibodies does not cause any undesirable interaction.

Furthermore, the antibodies of the present invention may be used in combination with other agents. The antibodies and other agents of the invention may be administered to the patient simultaneously or at different times.

Polynucleotides of the Invention

According to the present invention, a polynucleotide encoding the antibody of the present invention, which is used as an active ingredient of the above-described prophylactic/therapeutic agent or immunoglobulin fragment composition is provided. As an example, the polynucleotide is a polynucleotide encoding a polypeptide containing an amino acid sequence identical or substantially identical to the amino acid sequence represented by SEQ ID NO: 4, and preferably comprising an amino acid sequence identical or substantially identical to the amino acid sequence represented by SEQ ID NO: 4, more preferably a polypeptide with completely the same sequence represented by SEQ ID NO: 4. The polynucleotide encoding the antibody of the present invention may be DNA or RNA, or may be a DNA/RNA chimera, preferably DNA. Also, the polynucleotide may be double-stranded or single-stranded. When double stranded, it may be double stranded DNA, double stranded RNA or a hybrid of DNA:RNA. When single-stranded, it may be the sense strand (i.e., the coding strand) or the antisense strand (i.e., the non-coding strand).

Any DNA encoding the antibodies of the present invention contains, for example, a nucleotide sequence that hybridizes with DNA containing the nucleotide sequence shown in SEQ ID NO: under high stringency conditions, and encoding a protein having substantially the same activity as the protein containing the amino acid sequence shown in SEQ ID NO: 4 can be used as DNA encoding the antibodies of the present invention.

As the DNA capable of hybridizing under the high stringency condition with the base sequence represented by SEQ ID NO: 3, for example, DNA with homology (homology) of about 50% or more, preferably about 60% or more, more preferably about 70% or more, much more preferably about 80% or more, particularly preferably about 90% or more, most preferably about 95% or more with the base sequence represented by SEQ ID NO: 3 are used.

The homology of the base sequence in the present specification can be determined, for example, using the homology calculation algorithm NCBI BLAST (National Center for Biotechnology Information Basic Local Alignment Search Tool) under the following conditions (expected value=10; allow gaps; filtering=ON Match score=1; mismatch score=−3). As another algorithm for determining the homology of base sequences, the above-mentioned homology calculation algorithm for amino acid sequences is preferably exemplified as well.

The hybridization can be carried out according to a method known per se or a method analogous thereto, for example, a method described in Molecular Cloning 2nd ed. (J. Sambrook et al., Cold Spring Harbor Lab. Press, 1989). In addition, when using a commercially available library, it can be performed according to the method described in the attached instruction manual. More preferably, it can be performed according to high stringency conditions.

High stringency conditions include, for example, sodium concentration of from about 19 to about 40 mM, preferably from about 19 to about 20 mM, the temperature is from about 50 to about 70° C. and preferably from about 60 to about 65° C. Particularly, the sodium salt concentration is preferably about 19 mM and the temperature is about 65° C. One skilled in the art can easily adjust the desired stringency by changing the salt concentration of the hybridization solution, the temperature of the hybridization reaction, and the probe concentration, the length of the probe, the number of mismatches, and the time of hybridization reaction, the salt concentration of the washing liquid, the temperature of washing, and the like.

In SEQ ID NO: 3, a sequence encoding six histidine residues constituting a His tag is added to the 3'-end (778th to 795th bases of SEQ ID NO: 3). Therefore, as polynucleotides encoding the antibodies of the present invention, the polynucleotides preferably comprise a nucleotide sequence containing at least the 1st to 777th bases of SEQ ID NO: 3 (or a nucleotide sequence having the above-mentioned homology to the sequence). From the same viewpoint, as the antibodies of the present invention, antibodies consisting of a polypeptide comprising an amino acid sequence identical or substantially identical ("substantially identical" means the same as described above) to the amino acid sequence comprising the first to 259th amino acids of SEQ ID NO: 4 are also preferred.

The invention also provides vectors containing the polynucleotide of the present invention as described above. The vectors may be used as a preventive and/or therapeutic agent for infectious diseases or inflammatory diseases which itself contains as an active ingredient and may be used for producing the antibodies of the present invention.

As the above-mentioned vectors, generally, plasmids or viral vectors carrying DNA encoding the antibody of the present invention are common. Persons skilled in the art can appropriately produce vectors having a desired DNA by general genetic engineering techniques. Usually, various commercially available vectors can be used.

The vectors of the present invention are useful for retaining the polynucleotides of the present invention in host cells or for expressing the antibodies of the present invention.

The polynucleotides of the present invention are usually carried (inserted) into suitable vectors and introduced into a host cell. The vectors are not particularly limited as long as they stably hold the inserted DNA. For example, if *E. coli* is used as host cells, pBluescript™ vector (an expression vector manufactured by Stratagene) etc. is preferable as a cloning vector, but various commercially available vectors can be used. In addition, when using vectors for the purpose of producing the antibodies of the present invention, expression vectors are particularly useful. The expression vectors are not particularly limited as long as they are vectors that express polypeptides in test tubes, in *E. coli*, in cultured cells, and in an organism individual, but for example, pBEST vectors (Promega) for in vitro expression, *E. coli* And pME18S-FL3 vectors (GenBank Accession No. AB009864) for cultured cells, pME18S vectors (Mol Cell Biol. 8: 466-472 (1988)) for cultured organisms, etc., can be illustrated. Insertion of the polynucleotide of the present invention into a vector can be carried out in a conventional manner, for example, by a ligase reaction using restriction sites, or by the In-fusion® (a ligation-independent method for cloning of PCR products) method (Takara Bio).

The host cells are not particularly limited, and various host cells may be used depending on the purpose. Cells for expressing the antibodies of the present invention include bacterial cells (e.g., *Streptococcus, Staphylococcus, E. coli, Streptomyces, Bacillus subtilis*), insect cells (e.g., *Drosophila* S2 and *Spodoptera* SF9), animal cells (e.g., Examples: CHO, COS, HeLa, C127, 3T3, BHK, HEK 293, Bowes melanoma cells) and plant cells can be exemplified. Vector introduction into host cells can be carried out by known methods, for example, calcium phosphate precipitation, electroporation (Current protocols in Molecular Biology edit. Ausubel et al. (1987) Publish. John Wiley & Sons. Sections 9.1-9.9), lipofection (GIBCO-BRL). and microinjection.

An appropriate secretion signal can be incorporated into the polypeptides of interest in order to secrete the polypeptides expressed in host cells into the lumen of the endoplasmic reticulum, into the periplasmic space, or into the extracellular environment. These signals may be endogenous or xenogenous to the polypeptides of interest.

Recovery of the polypeptides in the above production method involves recovering the culture medium when the polypeptide of the present invention is secreted into the culture medium. If the polypeptides of the present invention are produced intracellularly, the cells are first lysed and then the polypeptides are recovered.

To recover and purify the polypeptides of the invention from recombinant cell cultures, known methods, e.g., ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography can be used.

The protein (APOA2) of the present invention is expressed in patients who are successfully treated with the antibody of the present invention. In addition, inhibition of APOA2 activity can prevent or treat infectious diseases or inflammatory diseases. Therefore, a compound that inhibits the activity of APOA2 or its salt derivatives can be used as a preventive and/or therapeutic agent for infectious diseases or inflammatory diseases.

Thus, the protein (APOA2) of the present invention is useful as a reagent for screening compounds that inhibit the activity of the protein or its salt derivatives.

That is, according to another embodiment of the present invention, screening methods for compounds that inhibit the activity of the protein or its salt derivatives using the proteins of the present invention are provided.

When the compound or its salt derivatives inhibiting the activity of the protein of the present invention is screened, screening methods are:

(a-1) methods of comparing activities of isolated proteins of the present invention in the presence and absence of a test substance, (a-2) methods of culturing cells having the ability to produce the protein of the present invention in the presence and absence of a test substance and then comparing the activity of the protein of the present invention under both conditions.

The protein of the present invention used in the screening method of the above (a-1) can be isolated and purified using the above-mentioned method of producing the protein of the present invention or its partial peptides.

The cells having the ability to produce the proteins of the present invention used in the screening method of the above (a-2) are not particularly limited as long as they are human or other warm-blooded animal cells naturally expressing them or biological samples (blood, tissues, organs, etc.) containing them. In the case of blood, tissues, organs, etc. derived from non-human animals, they may be isolated from a living body and cultured in vitro. Alternatively, a test substance is administered to a living body and then those biological samples are isolated from the body a predetermined time after the administration.

Examples of cells having the ability to produce the proteins of the present invention include various transformants produced by the above-mentioned genetic engineering techniques.

Test substances include, for example, proteins, peptides, non-peptide compounds, synthetic compounds, fermentation products, cell extracts, plant extracts, animal tissue extracts. These substances may be novel or known.

The activity of the protein of the present invention in the screening methods described above (a-1) and (a-2) can be measured by conventional methods.

The screening kits of the present invention include the proteins of the present invention or their partial peptides (hereafter, simply referred to as "the proteins of the present invention"). The proteins of the present invention may be isolated/purified using any of the methods described above or may be provided in the form of cells (warm-blooded animal cells) producing them.

The screening kits of the present invention can also include the antibodies of the present invention in order to measure the expression amount of the proteins of the present invention in cells producing the proteins.

The screening kits can optionally include, in addition to the above, reaction buffers, blocking solutions, washing buffers, labeling reagents, label detection reagents, etc.

Substances inhibiting the activity of the protein of the present invention (either free or salt forms), obtained by the screening methods or screening kits of the present invention, may be useful as low-toxic and safe medicines for preventing/treating infectious diseases or inflammatory diseases.

When the compounds or their salt derivatives obtained by the screening methods or screening kits of the present invention are used as medicines for preventing/treating diseases described above, they can be formulated according to conventional means.

In the present specification, when bases, amino acids and the like are indicated by abbreviations, they are based on abbreviations according to IUPAC-IUB Commission on Biochemical Nomenclature or common abbreviations in the field. In addition, when there is an optical isomer of an amino acid, it is assumed to indicate an L-isomer unless otherwise specified.

As described above, inhibition of the activity of the protein (APOA2) of the present invention makes it possible to prevent and/or treat infectious diseases or inflammatory diseases. Thus, the protein of the present invention (APOA2) is a cause of infectious or inflammatory diseases. From this, according to another aspect of the present invention, inducers for infectious disease or inflammatory disease, which comprises apolipoprotein A2 (APOA2) as an active ingredient, are provided.

Furthermore, according to still another embodiment of the present invention, methods of producing animal disease models for infectious diseases or inflammatory diseases, comprising the step of administering apolipoprotein A2 (APOA2) to non-human, non-transgenic animals are provided. In addition, according to still another embodiment of the present invention, pathological model animals of infectious diseases or inflammatory diseases produced by the above-mentioned production method are also provided.

The method for producing pathological model animals of infectious diseases or inflammatory diseases according to one embodiment of the present invention comprises the step of administering apolipoprotein A2 (APOA2) to non-human, non-transgenic animals. By configuring in this way, it is possible to induce the experimental animal to have symptoms specific to infectious diseases or inflammatory diseases. In addition, since it is as having mentioned above about a specific disease, detailed description is omitted here.

The non-transgenic animals used in the method for producing pathological model animals according to the present embodiment refers to so-called wild-type animals which are not transgenic animals. Here, transgenic animals are animals into which foreign DNA has been introduced into the genome, and also includes a knockout animal or the like in which the function of a specific gene is not expressed by introducing an artificially engineered gene. Also, transgenic animals include both those with heritable germline DNA changes and those with non-heritable somatic DNA changes. That is, the pathological model animals concerning this form are produced based on wild type animals. There have been few examples of pathological animal models for infectious diseases or inflammatory diseases, which were derived from wild-type animals. As specific animals, any mammals except human can be used. Examples of such animals include rodents such as guinea pigs, mice, rats, and hamsters, non-human primates such as monkeys, chimpanzees and orangutans, rabbits, bovine, goats, sheep and porcine, but not limited to these. Rodents, particularly mice, are preferable.

In the method of producing a pathological model animal according to the present embodiment, the administration route of apolipoprotein A2 (APOA2) is not particularly limited. Whether orally or parenterally administered, any conventionally known administration routes, such as oral, intraperitoneal, intravenous, intraarterial, intramuscular, subcutaneous, intradermal, inhalation, intragastric, enteral, transdermal, etc. may be exemplified, but are not limited thereto.

Apolipoprotein A2 (APOA2) may be administered alone, or in combination with a suitable pharmaceutically acceptable carrier or diluent as long as the effect of apolipoprotein A2 (APOA2) is not impaired. Therefore, administration components may include various ingredients used for medicines and cosmetics, and it can be prepared and used as a preparation which has various dosage forms.

The dose, frequency of administration, and administration period of apolipoprotein A2 (APOA2) can be appropriately set according to the type of animal, strain, age, sex difference, etc. As mice, FVB/N, Balb/c and C57BL/6, which are widely used as experimental animals, are preferable, but not limited thereto. A single administration may be adequate if the desired symptoms develop in a single dose, and administration may be continued until the desired onset occurs.

The method for confirming whether or not the produced disease model animal has developed infectious diseases or inflammatory diseases can be performed based on known methods. For example, the onset of vasculitis, as shown in examples described later, can be confirmed by examining the presence of pathological changes specific to the above-mentioned diseases by the observation of tissues, such as kidney, spleen and lung of a model animal under the microscope. The onset may also be confirmed by evaluating the animal's Urinary Score or detecting or measuring various components in the blood collected from the animal.

And as another embodiment of this invention, pathological model animals produced by the preparation method of the pathological model animal of the infectious disease or inflammatory disease mentioned above are also provided. The pathological model animals of the infectious disease or inflammatory disease provided by the present embodiment are non-transgenic animals, i.e., one produced by administering apolipoprotein A2 (APOA2) to wild-type animals, and indicate symptoms specific to the infectious disease or inflammatory disease. Therefore, the pathological model animals provided by the present embodiment can be used for analysis of the onset and pathogenesis mechanism of an infectious disease or an inflammatory disease, in particular, intractable vasculitis, and for evaluation and screening of treating/preventing methods for these diseases and therapeutic/preventive agents.

Moreover, according to the other embodiment of the present invention, the screening method of the preventive and/or therapeutic agent of an infectious disease or an inflammatory disease is also provided. For example, a test substance which is a candidate for a preventive and/or therapeutic agent for an infectious disease or an inflammatory disease can be administered to the above-described pathological model animal to evaluate improvement and elimination of symptoms. Here, any test substances may be used as long as they are candidate substances for infectious disease or inflammatory disease, regardless of whether they are in vivo substances, genetically modified substances, chemically synthesized compounds, etc., and the test substances are not limited to these. Also, they may be administered alone, but may be formulated and administered in combination with a suitable pharmaceutically acceptable carrier or diluent. Administration of the test substances may be performed according to any known administration routes and may be either oral or parenteral administration. Therefore, oral, intraperitoneal, intravenous, intraarterial, intramuscular, subcutaneous, intradermal, inhalation, intragastric, enteral, transdermal, etc., can be exemplified, but not limited thereto. It may be set in consideration of the properties of the test substances, particularly pharmacokinetic properties and solubility. The dose, frequency and period of administration of the test substances can be appropriately set according to the type of animal, strain, age, sex, etc., and the type of test substances.

Evaluation of the improvement and elimination of symptoms in the method for screening a preventive and/or therapeutic agent for an infectious disease or an inflammatory disease in this embodiment can be performed in the same way as those employed in the various indexes described above and the examples described later. Then, when the administration of the test substance improves or eliminates the symptoms, the test substance can be evaluated as a preventive and/or therapeutic agent for infectious disease or inflammatory disease. In addition, as a negative control, a pathological model animal to which a formulation having the same composition except the test substance is administered or no test substance is administered can be used. The negative control animals can be compared to the animals receiving the test substance for improvement and elimination of symptoms. And, for example, when the symptom in the animal to which the test substance is administered is improved over the negative control animal to which the test substance is not administered, the test substance can be evaluated as an agent for preventing and/or treating infectious disease or inflammatory disease.

EMBODIMENTS

Hereinafter, the present invention will be described in detail by way of examples, but the present invention is not limited to the following examples. In the following examples, all blood samples were collected from humans after informed consent was made to confirm the intention of the blood donor.

Embodiment-1

1. Identification of the Target Molecule of the Recombinant Human ScFv Antibody (VasSF)

The search for antigens targeted by recombinant human ScFv (VasSF) consisting of amino acid sequence shown in SEQ ID NO: (identical to SEQ ID NO: 4 in the present specification) of Japanese Patent Application Laid-Open No. 5, which depicts that various therapeutic effects have been shown in Japanese Patent Application Laid-Open No. 5 against intractable vasculitis model mice, was attempted as follows.

First, for identification of an antigen targeted by a specific antibody, there are roughly two methods as shown in FIG. 1A, but identification of a target molecule is generally extremely difficult.

In the present embodiment, the present inventors searched for the target antigen of VasSF by using each of the following three techniques, and finally, the present inventors succeeded in identifying target antigens by narrowing down candidate substances using tosylactivated Dynabeads® (superparamagnetic particles) and MS/MS method.

1-1. Identification by ProteoSeek™ (an Albumin/Igg Removal Kit) Method

The present inventors prepared plasma from healthy individuals as a sample, treated it with ProteoSeekm Albumin/

IgG Removal Kit (PIERCE), and then attempted to identify the target antigen by SDS-PAGE and Western blotting using the following primary to quaternary antibodies.

Primary antibody: VasSF

Secondary antibody: anti-human IgG F(ab)$_2$ antibody (Rockland)

Tertiary antibody: anti-rabbit IgG goat antibody (alkaline phosphatase labeled, Invitrogen)

Quaternary antibody: anti-goat IgG rabbit antibody (alkaline phosphatase labeled, Jackson)

Figure 1B:
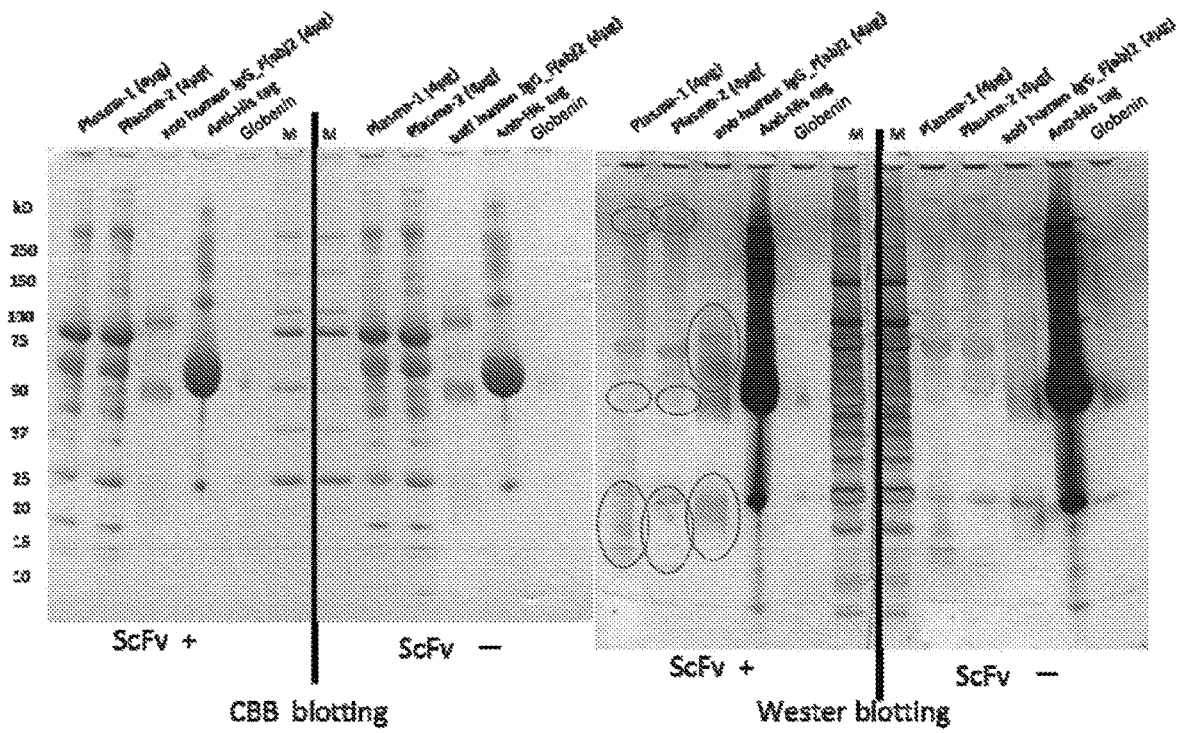
FIG. 1B A photograph showing the results of attempting to identify the target antigen by the ProteoSeek™ (an albumin/IgG removal kit) method in Embodiment 1.

These results are shown in FIG. 1B. The photograph on the left of FIG. 1B shows the result of Coomassie brilliant blue (CBB) staining, and the photograph on the right shows the result of Western blotting. Although the reaction was found at the circled site on the right side of the photograph, a large number of target antigen candidate spots overlapped. Therefore, this experiment did not lead to the identification of the target antigen.

1-2. Identification by HiTrap® (a Chromatography Column) NHS-Activated HP Column (GE Healthcare)

HiTrap® (a chromatography column) NHS-activated HP column (GE Healthcare) with a bed volume of 1 mL was prepared. Five milliliters (2 mg) of a 0.4 mg/mL solution of VasSF was weighed out and concentrated about 40-fold using Amicon 10K. It was then diluted with coupling buffer and allowed to bind to the column prepared above.

Then, plasma from healthy individuals prepared as a sample was treated with the above-mentioned column, and identification of the target antigen was attempted by CBB staining, silver staining, and Western blotting.

Figure 1C:
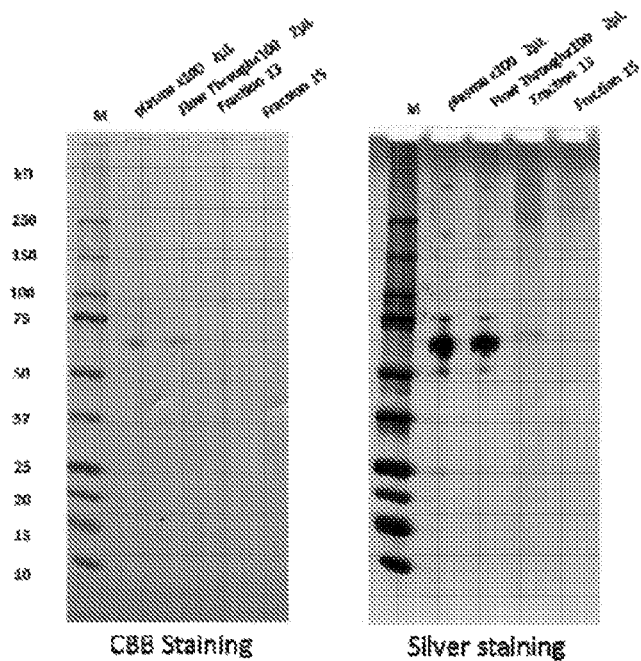
FIG. 1C A photograph showing the results of attempting to identify the target antigen by the HiTrap® (a chromatography column) using an NHS-activated HP column in Embodiment 1.

The staining results of the sample-bound column are shown in FIG. 1C. As shown in FIG. 1C, although CBB staining (left in FIG. 1C) was hardly detectable, silver staining (middle in FIG. 1C) could detect a slight amount. In Western blotting (right in FIG. 1C), a thick band was observed around 10 kDa. However, since a large number of target antigen candidate spots overlapped in this experiment, the identification of the target antigen was not achieved even in this experiment.

1-3. Identification by Tosylactivated Dynabeads® (Superparamagnetic Particles)

According to the attached protocol, ligand-coated beads were prepared by mixing and reacting Dynabeads® (superparamagnetic particles) Tosylactivated (25 mg) in 0.1 M sodium borate buffer using 1 mg of VasSF as a ligand. The coated beads were then washed 5 times with PBS (containing 0.05% Tween 20).

On the other hand, 3 mL of human plasma (using EDTA-2K as an anticoagulant at the time of blood collection) diluted 10-fold with PBS, and centrifugally filtered with an ultrafiltration membrane of 50 kDa was used as a sample.

This sample was mixed with 25 mg of the above coated beads and allowed to react at room temperature with rotation for 1 hour. After removing plasma, the beads were washed three times with PBS (containing 0.05% Tween 20).

Figure 2:
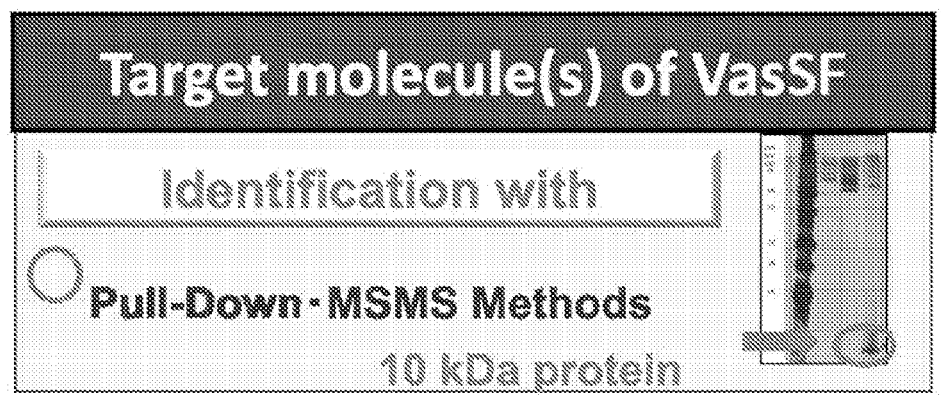
FIG. 2 A photograph showing the results of attempting to identify the target antigen by the HiTrap® (a chromatography column) using the tosyl group activation of DYNABEADS® (superparamagnetic particles) in Embodiment 1.

The fraction bound to the coated beads was then eluted with elution buffer (0.1 M glycine-HCl, pH 2.7) and then neutralized with 1/10 volume of neutralization buffer (1 M Tris HCl, pH 9.0). The fraction eluted in this manner was subjected to SDS-PAGE. Here, a photograph showing the result of silver staining of this SDS-PAGE is shown in FIG. 2. As shown in the photograph of FIG. 2, the band (spot) of about 10 kDa was cut out.

Embodiment 2

2. Search for the Target Antigen Candidate in the Spot Using MS/MS Ion Search

Figure 3:
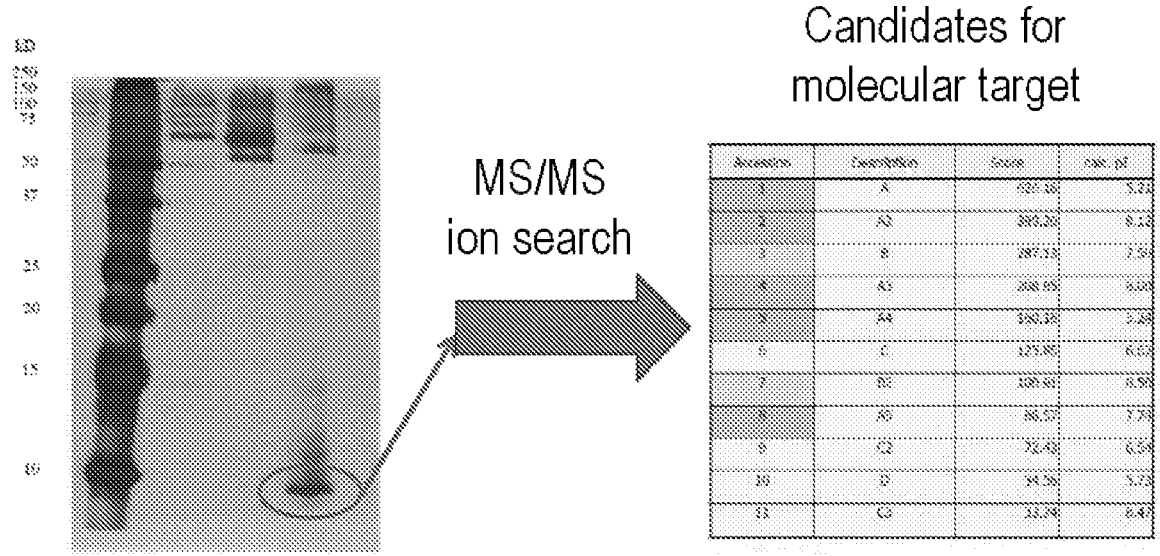
FIG. 3 The left is the same photograph as FIG. 2, and the right panel shows a table of 11 kinds of candidate molecules hit by the MS ion search.

The spot obtained in FIG. 2 was cut out with a cutter (left in FIG. 3). Next, MS/MS spectrum of the peptide mixture obtained by protease digestion was obtained by a method of selecting ions derived from specific peptides in a mass spectrometer. The score was calculated from the obtained MS/MS spectrum and all protein data registered in the database (Table 1). As a result, eleven types of proteins listed in Table 1 shown below were hit as candidate molecules for the target antigen (the table in the right of FIG. 3 describes the same one by an abbreviation).

TABLE 1

Candidate molecules detected by MS/MS ion search

| Accession | Description | Score | Coverage | # Peptides |
|---|---|---|---|---|
| P13645 | Keratin, type I cytoskeletal 10 OS = Homo sapiens GN = KRT10 PE = 1 SV = 6 - [K1C10_HUMAN] | 626.1614488 | 21.06 | 13 |
| P04264 | Keratin, type II cytoskeletal 1 OS = Homo sapiens GN = KRT1 PE = 1 SV = 6 - [K2C1_HUMAN] | 389.2013617 | 15.22 | 9 |
| P01859 | Ig gamma-2 chain C region OS = Homo sapiens GN = IGHG2 PE = 1 SV = 2 - [IGHG2_HUMAN] | 287.13 | 7.98 | 2 |
| P35908 | Keratin, type II cytoskeletal 2 epidermal OS = Homo sapiens GN = KRT2 PE = 1 SV = 2 - [K22E_HUMAN] | 208.85 | 8.29 | 4 |
| P35527 | Keratin, type I cytoskeletal 9 OS = Homo sapiens GN = KRT9 PE = 1 SV = 3 - [K1C9_HUMAN] | 160.1756668 | 6.1 | 3 |
| P02652 | Apolipoprotein A-II OS = Homo sapiens GN = APOA2 PE = 1 SV = 1 - [APOA2_HUMAN] | 125.85 | 21 | 3 |
| P01763 | Ig heavy chain V-III region WEA OS = Homo sapiens PE = 1 SV = 1 - [HV302_HUMAN] | 100.9136683 | 9.65 | 1 |
| P13647 | Keratin, type II cytoskeletal 5 OS = Homo sapiens GN = KRT5 PE = 1 SV = 3 - [K2C5_HUMAN] | 86.56619075 | 5.42 | 3 |
| P81605 | Dermcidin OS = Homo sapiens GN = DCD PE = 1 SV = 2 - [DCD_HUMAN] | 72.43 | 12.73 | 2 |
| Q8IWZ3 | Ankyrin repeat and KH domain-containing protein 1 OS = Homo sapiens GN = ANKHD1 PE = 1 SV = 1 - [ANKH1_HUMAN] | 34.56 | 0.28 | 1 |
| P02654 | Apolipoprotein C-I OS = Homo sapiens GN = APOC1 PE = 1 SV = 1 - [APOC1_HUMAN] | 33.74 | 10.84 | 1 |

Embodiment 3

3. Therapeutic Effect of Polyclonal Antibodies Against Candidate Molecules for the Target Antigen 1) Among the 11 candidate molecules listed in the above table, preparation of polyclonal antibodies was attempted for five molecules assumed to be present in blood: Ig gamma-2 chain C region, apolipoprotein A-II, Ig heavy chain V-III, ankyrin repeat and KH domain-containing protein 1, and Apolipoprotein C-I.

2) Each antigen containing a recombinant human ApoAII antigen was mixed with an adjuvant and inoculated into a rabbit.

3) The respective antigens were inoculated 4 times into the rabbit every other week, and one week later, blood was collected to confirm that the antibody titer was sufficiently high by ELISA.

4) Blood samples were collected from highly immunized rabbits to separate plasma.

5) IgG was separated from plasma using protein G column.

6) Specific antibodies were separated and purified from the IgG fraction by an affinity column to which each antigen was bound.

7) The obtained polyclonal antibodies were administered to spontaneous onset model mice (SCG/Kj mice) of intractable vasculitis to determine the therapeutic effect of each antibody.

As a result of the above examination, only the polyclonal antibody prepared against Apolipoprotein A-II (apolipoprotein A2; APOA2) showed a remarkable therapeutic effect. From this, the target antigen of VasSF was finally identified as Apolipoprotein A-II (apolipoprotein A2; APOA2).

Embodiment 4

4. Therapeutic effect of the anti-APOA2 polyclonal antibody as antibody medicine for treatment of intractable vasculitis The anti-APOA2 polyclonal antibody that showed remarkable therapeutic effect in embodiment 3 described above was used by dissolving it in 1.5% D-mannitol solution containing 0.45% glycine (Gly) and 0.9% sodium chloride.

First, anti-APOA2 polyclonal antibodies are administered intraperitoneally to a 10-week-old SCG/Kj mice at a prescription of 10-40 mg/kg/day for 5 days by intraperitoneal administration (ip), and when the mice became 13-week-old, they were euthanatized with $CO_2$ gas. Then, MPO-ANCA (myeloperoxidase-specific anti-neutrophil cytotoxic antibody) value in serum which is an index of vasculitis, spleen weight, leukocyte count in peripheral blood, lymphocyte count, monocyte count, granulocyte count, the number of neutrophils and the number of platelets were measured, and the treatment effect was determined based on the results.

4-1. Methods 4-1-1) Husbandry of Mice

SCG/Kj mice are kept in an environment set to a light/dark cycle of 14L10D (light period 5:00-19:00, dark period 19:00-5:00), temperature 23±1° C., and humidity 50±5%. Feeds were radiation-sterilized CRF1 for small rodents (for special breeding, Oriental Yeast Co., Ltd.) until the experiment, and radiation-sterilized FR-2 for small rodents (for general breeding, Funabashi Farm) from the day before administration. Drinking water was clean water from a reverse osmosis (RO) drinking water treatment apparatus and supplemented with chlorine at a concentration of 0.3 to 2.0 ppm. Feeds and water were given ad libitum. The animal facility was supplied with clean air through HEPA filters and was limited to SPF animals only.

4-1-2) Treatment Method

The subject mice were subjected to a weekly urinalysis test from about 3 weeks ago, and divided into experimental groups based on the weight and the value of the urine occult blood and urine score on the day of administration. In the administration group, the sample was injected ip at 0.1 to 400 mg/kg for 5 days, and in the control group, Solvent (stabilizer: D mannitol, glycine, PBS) was injected ip for 5 days. The dose was calculated from the final measured body weight and adjusted to 0.33 mL per animal. After administration, weight measurement and urinalysis were performed twice a week.

4-1-3) Harvesting Materials

Clinical samples were collected from euthanized mice 3 weeks after administration.

1. Whole blood was collected from the heart under anesthesia $CO_2$ (dry ice). No heparin was used.

2. For examination of blood properties, 50 µL of blood was placed in a sampling tube containing EDTA-2K and saline: 250 µL and diluted. About 2 hours later, WBC, RBC, Hgb, Hct, MCV, MCH, MCHC, Plt were measured with an automatic measuring instrument (VetScan HMII ABAXIS, Union City, CA, USA).

3. Two slides of blood smear were prepared using peripheral blood or remained blood in blood-collecting syringe.

4. The residual blood was centrifuged and the serum was stored at −80° C. Then, it was sent to A-CLIP Research Institute, Inc. (for MPO-ANCA and cytokine (Bio-Plex) measurement).

5. After laparotomy and taking pictures, the spleen, heart, kidney, lung and skin are removed and processed, and the remaining whole body was immersed in 10% neutral buffered formalin solution (Wako Pure Chemical Industries, Ltd.: 060-01667).

Spleen: After weighing, 5 mm squares were taken for RNA later for RNA, and the remaining tissue was immersed in 10% neutral buffered formalin solution.

Lung: 5 mm squares were transferred into RNA Later for RNA, and the remaining tissue was immersed in 10% neutral buffered formalin solution after evacuation.

Kidney: After taking pictures, 5 mm squares were transferred into RNA Later for RNA, and the remaining tissue was divided and immersed into 10% neutral buffer formalin solution.

4-1-4) Measurement and Analysis

Spleen weight per body weight (%)

Crescent formation rate: Crescent formation rates in glomeruli (% crescent) were calculated by observation of 80 to 100 glomeruli on HE-stained tissue slides under the microscope.

4-1-5) Blood cell counts: leukocytes (WBC), lymphocytes (LYM), monocytes (MON), and neutrophils (GRA) were measured by VetScan (see above).

4-1-6) Biomarker Analysis in Serum

The quantification of MPO-ANCA and anti-moesin antibody, BUN was performed using ELISA.

Quantification of inflammatory cytokines and chemokines (shown below) in serum was performed by Bio-Plex (Bio-Rad) and expressed in pg/mL: Interleukin (IL)-1 alpha, IL-1 beta, IL-2, IL-3, IL-4, IL-5, IL-6, IL-9, IL-10, IL-12p40, IL-12p70, IL-13, IL-17, Eotaxin, G-CSF, GM-CSF, IFN-gamma, KC, MCP-1, MIP-1alpha, MIP-1beta, RANTES, TNF-alpha, IL-15, IL-18, FGF-basic, LIF, M-CSF, MIG, MIP-2, PDGF-BB, VEGF, IL6sR, IL-23.

4-2 Results
4-2-1) Reduction of Crescent Formation in the Renal Glomerulus

Figure 4:
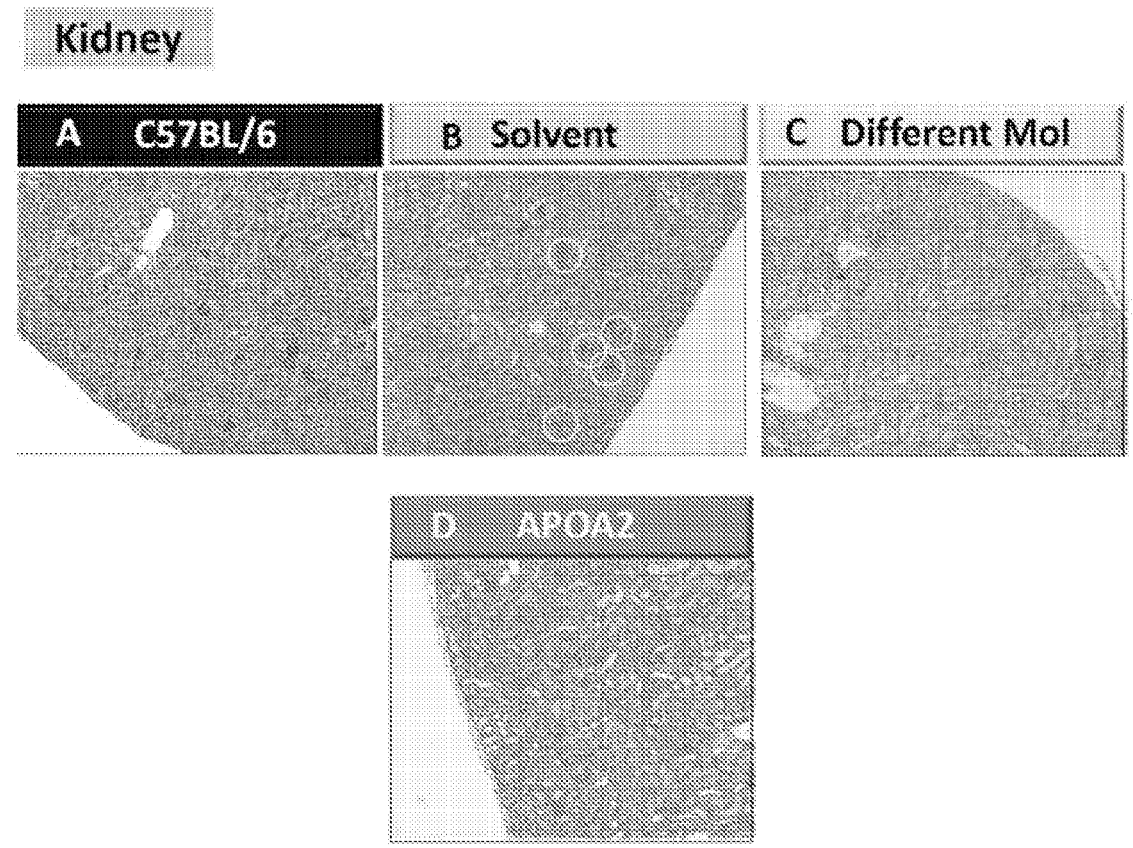
FIG. 4 A microscope photograph showing a result of evaluating a therapeutic effect of anti-APOA2 polyclonal antibody on the kidney tissues in Embodiment 4.
Figure 5:
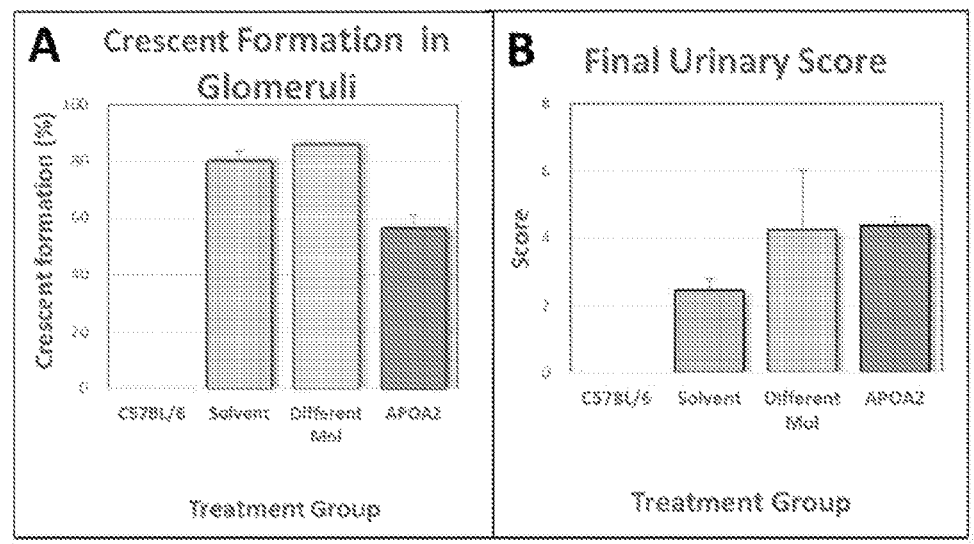
FIG. 5 A graph showing the results of evaluation of the therapeutic effect of anti-APOA2 polyclonal antibody the crescent formation in kidney glomerular tissues in Embodiment 4.

The main target tissues of intractable vasculitis, which is an autoimmune disease, are kidney, lung and spleen. First of all, there is a change in the glomerular histologic structure, which greatly affects the function of the kidney. In C57BL/6 healthy mice, a microscopic image in which Bowman's cavity of kidney glomerulus was formed is shown (FIG. 4A). On the other hand, microscopic images of kidney glomeruli of the untreated (Solvent-administered) group of the model mouse SCG/Kj formed crescents and renal dysfunction occurred (circled in FIG. 4B). The same situation was found for negative control administration (FIG. 4C). In addition, as a negative control, a molecule having a size of 55 kDa which is not recognized by the anti-Fab antibody (in the present specification, "Different Mol") purified in the process of purifying VasSF (ScFv) by the method described in Japanese Patent Application Laid-Open 3 was used. On the other hand, administration of anti-APOA2 polyclonal antibody to the model mouse SCG/Kj reduced the formation of kidney glomerulus crescents (FIG. 4D), and the formation rate was improved to about 50% (FIG. 5A).

Figure 6:
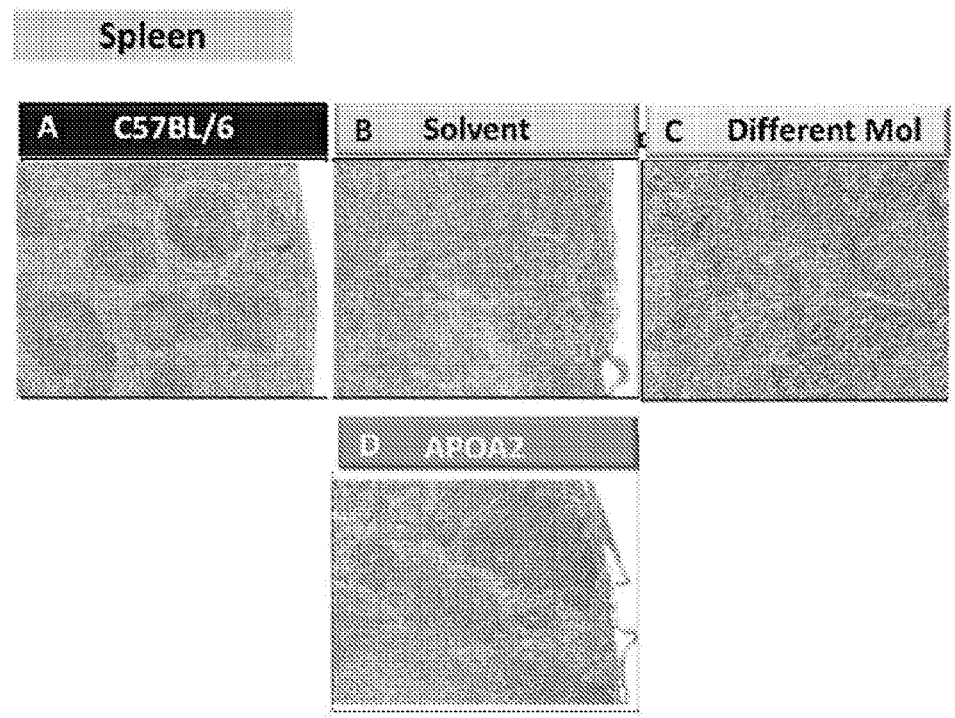
FIG. 6 A microscope photograph showing the results of evaluation of the therapeutic effect of anti-APOA2 polyclonal antibody on kidney tissues in Embodiment 4.

4-2-2) Therapeutic Effect of Anti-APOA2 Polyclonal Antibodies on the Spleen Tissue and its Weight Since intractable vasculitis is an autoimmune disease, a remarkable splenomegaly is observed in the model mice due to immune dysfunction (nonpatent literature 11). The microscopic image of the spleen of C57BL/6 healthy mice (FIG. 6A) shows that the white and red pulp were separated properly, but the microscope image (FIG. 6B) indicates that the white pulp and the red pulp were not separated in the spleen of the untreated (Solvent administration) group of the model mouse SCG/Kj. The same situation was found for administration of another molecule (Different Mol) from VasSF (FIG. 6C). On the other hand, administration of the anti-APOA2 polyclonal antibody to the model mouse SCG/Kj almost led their spleen to histologically normal one as seen in healthy mice (FIG. 6D).

Figure 7:
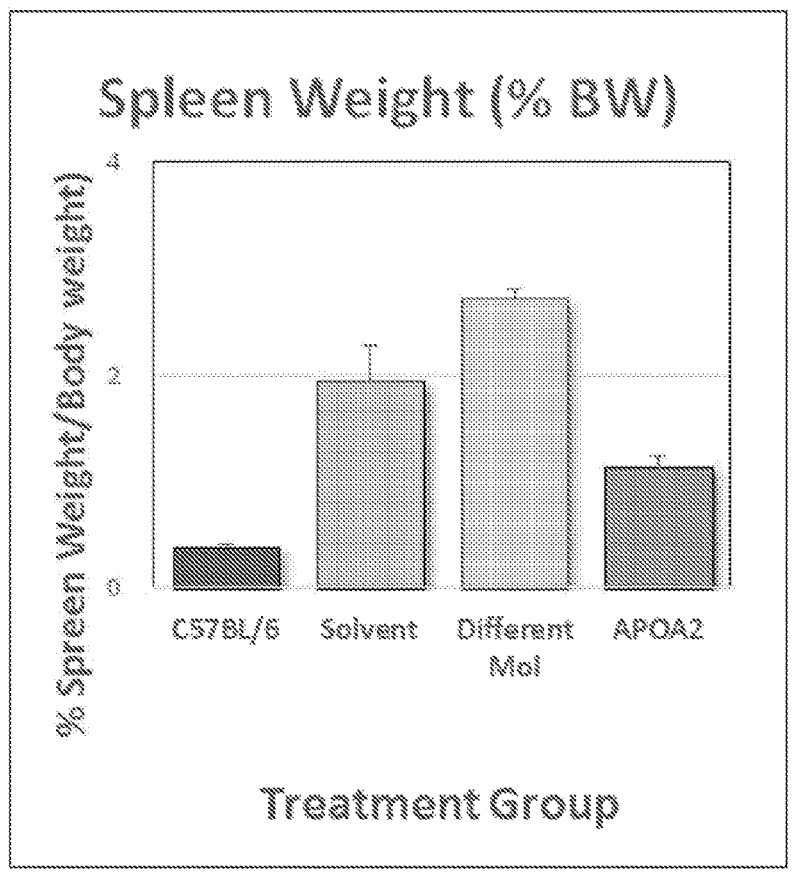
FIG. 7 A graph showing the results of evaluation of the therapeutic effect of anti-APOA2 polyclonal antibody on spleen weight in Embodiment 4.

As shown in FIG. 7, SCG/Kj model mice in the non-treated (Solvent administration) group had heavier spleens than C57BL/6 healthy mice. On the other hand, administration of the anti-APOA2 polyclonal antibody to SCG/Kj model mice reduced the spleen weight, although it did not fall to the value of the spleen weight of healthy mice. Administration of a molecule different from VasSF (Different Mol) did not reduce the spleen weight.

Figure 8:
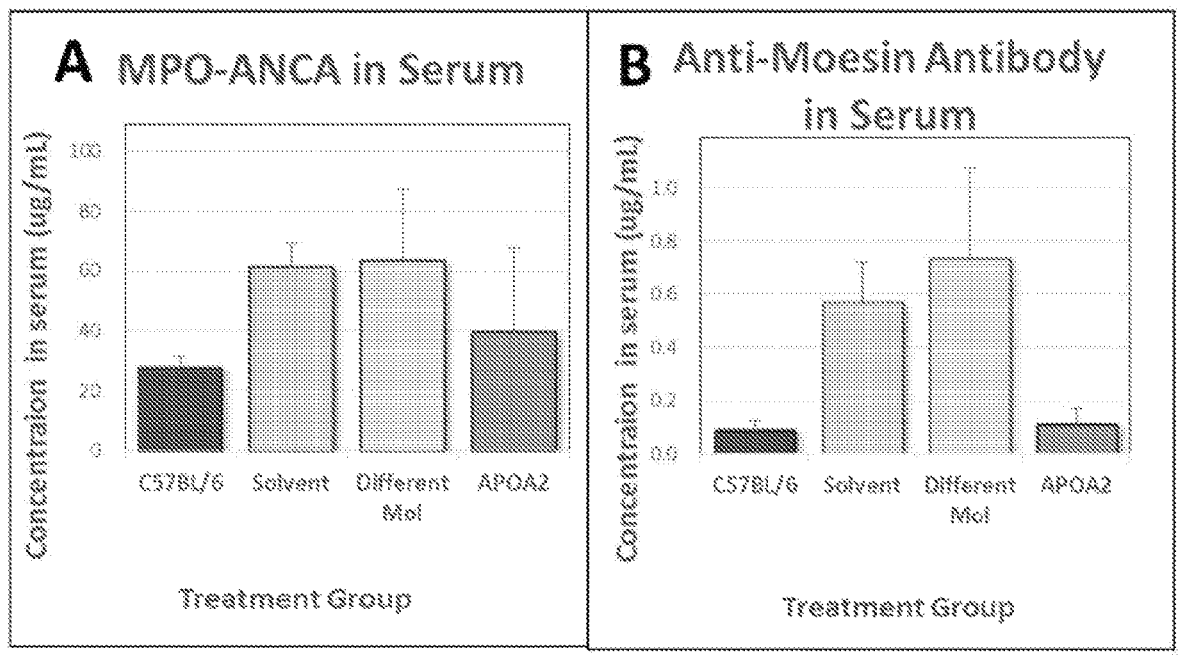
FIG. 8 A graph showing the results of evaluation of the therapeutic effect of anti-APOA2 polyclonal antibody on levels of MPO-ANCA and anti-moesin antibodies in sera in Embodiment 4.
Figure 9:
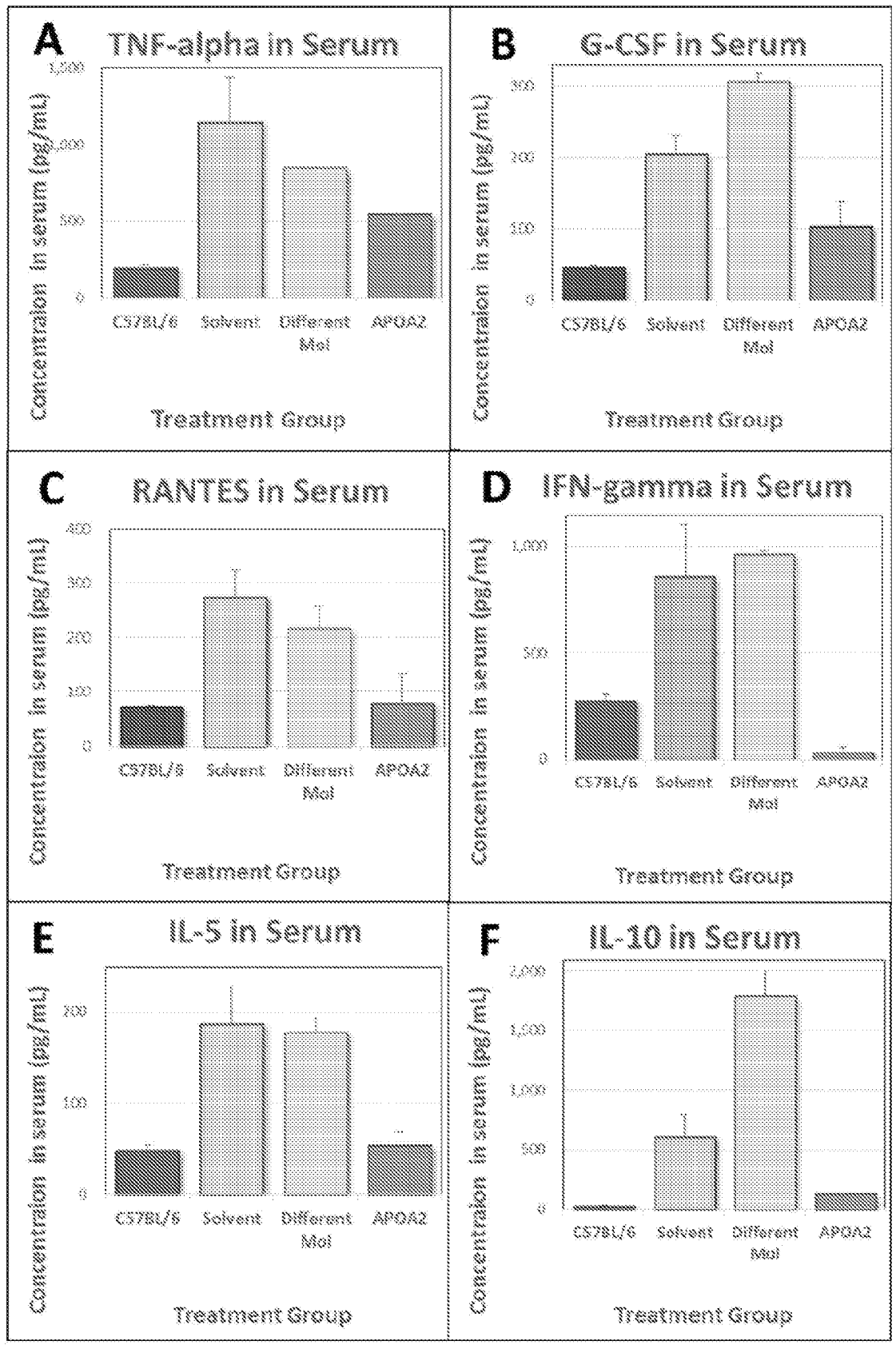
FIG. 9 A graph showing the results of evaluation of the therapeutic effect of anti-APOA2 polyclonal antibody on levels of cytokines and chemokines in sera in Embodiment 4.

4-2-3) Therapeutic Effect of Anti-APOA2 Polyclonal Antibodies on Serum Biomarkers of Intractable Vasculitis: MPO-ANCA and Anti-Moesin Antibodies Since intractable vasculitis is an autoimmune disease, the therapeutic effects of anti-APOA2 polyclonal antibodies on the levels of serum biomarkers used in clinical examination, i.e., MPO-ANCA and a new biomarker, anti-moesin antibody discovered by Kazuo Suzuki et al. (nonpatent literature 4), were examined. Compared with the untreated (Solvent administration) group and the administration group of another molecule (Different Mol) to VasSF to SCG/Kj model mice positive for MPO-ANCA, administration of the anti-APOA2 polyclonal antibody substantially improved the levels of serum MPO-ANCA and anti-moesin antibody in SCG/Kj model mice to similar ones in healthy mice (FIGS. 8A and 8B).

4-2-4) Therapeutic Effects of Anti-APOA2 Polyclonal Antibodies on Serum Levels of Cytokines and Chemokines Since histological normalization and weight reduction of the spleen, and reduction of serum autoantibodies (MPO-ANCA and anti-Moesin antibody) to near normal levels by anti-APOA2 polyclonal antibody were confirmed, serum levels of inflammatory cytokines serving as markers of inflammation were measured in pg/mL with Bio-Plex (Bio-Rad). Out of IL-1alpha, IL-1beta, IL-2, IL-3, IL-4, IL-5, IL-6, IL-9, IL-10, IL-12p40, IL-12p70, IL-13, IL-17, Eotaxin, G-CSF, GM-CSF, IFN-gamma, KC, MCP-1, MIP-1 alpha, MIP-1 beta, RANTES, TNF-alpha, IL-15, IL-18, FGF-basic, LIF, M-CSF, MIG, MIP-2, PDGF-bb, VEGF, IL6sR, and IL-23, almost all cytokine/chemokine levels increased in non-treated (Solvent administration) group of SCG/Kj model mice. On the other hand, the levels of TNF-alpha, G-CSF, RANTES, IFN-gamma, IL-5 and IL-10 in the SCG/Kj model mice were improved by administration of anti-APOA2 polyclonal antibody (FIGS. 9A to 9F).

LEGEND

IL-1a: interleukin-1 alpha
IL-1b: interleukin-1 beta
IL-2: interleukin-2
IL-3: interleukin-3
IL-4: interleukin-4
IL-5: interleukin-5
IL-6: interleukin-6
IL-9: interleukin -9 (interleave -9)
IL-10: interleukin -10 (interleave -10)
IL-12p40: interleukin-12 subunit p40
IL-12p70: interleukin-12 subunit p70
IL-13: interleukin-13
IL-17: interleukin-17
EOTAXIN: eotaxin
G-CSF: granulocyte colony stimulating factor
GM-CSF: granulocyte/macrophage colony stimulating factor
IFN-a: interferon gamma
Kc: keratinocytes derived chemokines
MCP-1: monocyte chemotaxis protein-1
MIP-1a: macrophage inflammatory protein-1 alpha
MIP-1b: macrophage inflammatory protein-1 beta
RANTES: regulated on activation, normal T-cell expressed and secreted
TNF-a: tumor necrosis factor-alpha
IL-15: interleukin-15
L-18: interleukin-18
FGF-basic: basic-fibroblast growth factor-basic
LIF: leukemia-inhibiting factor
M-CSF: macrophage colony stimulating factor
Mig: interferon gamma-inducible monocaine
MIP-2: macrophage inflammatory protein-2
PDGF-BB: platelet-derived growth factor-BB
VEGF: vascular endothelial growth factor
IL-6sr: interleukin -6 soluble receptor
IL-23: interleukin-23

Figure 10:
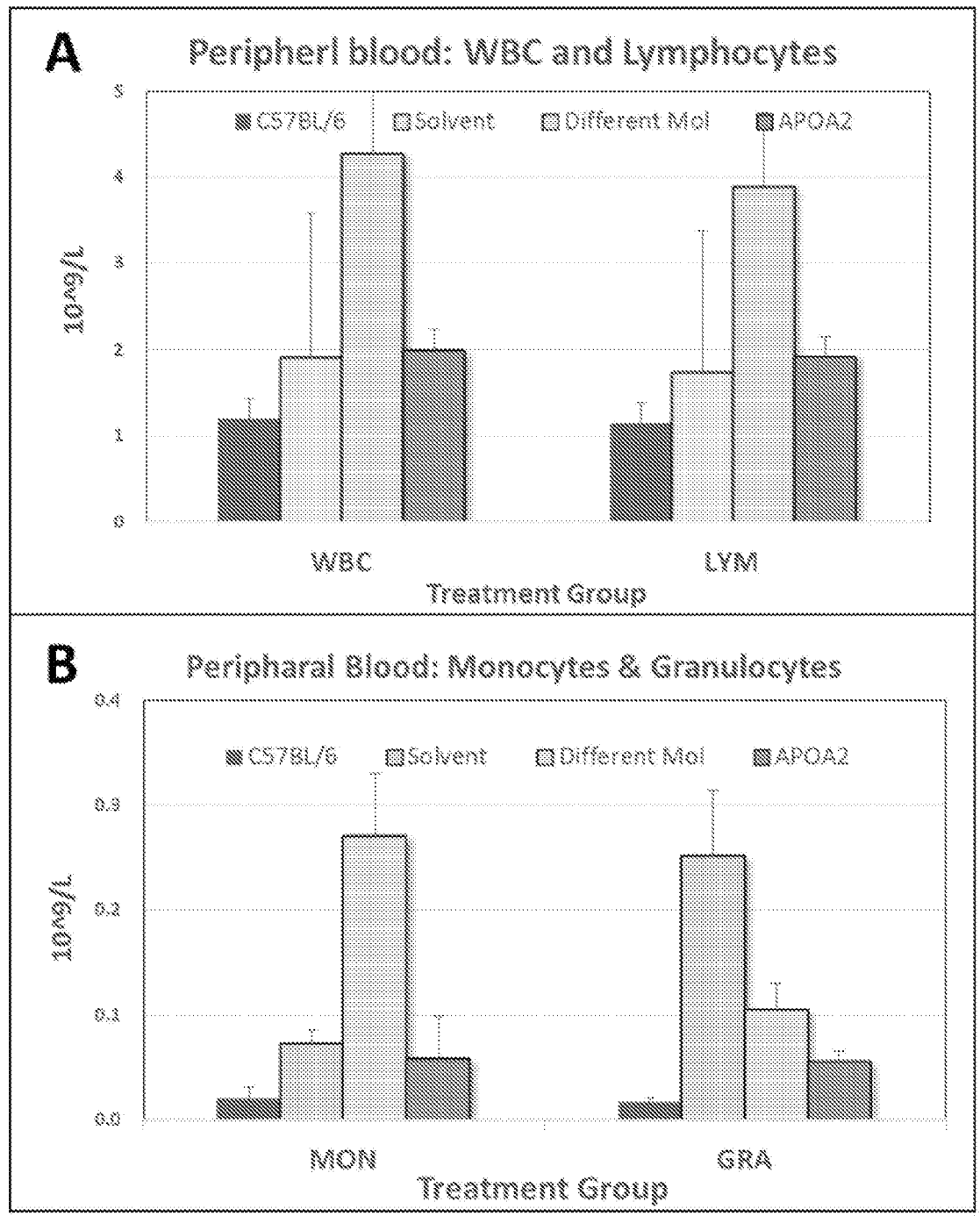
FIG. 10 A graph showing the results of evaluation of the therapeutic effect of anti-APOA2 polyclonal antibody on levels of white blood cells in the peripheral blood in Embodiment 4.

4-2-5) Therapeutic effects of anti-APOA2 polyclonal antibodies on white blood cell counts in the peripheral blood Intractable vasculitis is an autoimmune disease, and SCG/Kj model mice had splenomegaly and increased serum levels of autoantibodies MPO-ANCA, anti-moesin antibodies, inflammatory cytokines and chemokines. Like VasSF, anti-APOA2 Polyclonal antibodies directed these towards normalization. From these results, the influence on leukocytes in peripheral blood was examined. There were no changes in the total white blood cell count (WBC), the number of lymphocytes (LYM), and the number of monocytes (MON) (FIGS. 10A, and 10B). However, the neutrophil count (GRA) improved to almost the value of healthy mice by administration of the anti-APOA2 polyclonal antibody (FIG. 10B).

4-2-6) Microscopic Images of Lung Tissues

Figure 11:
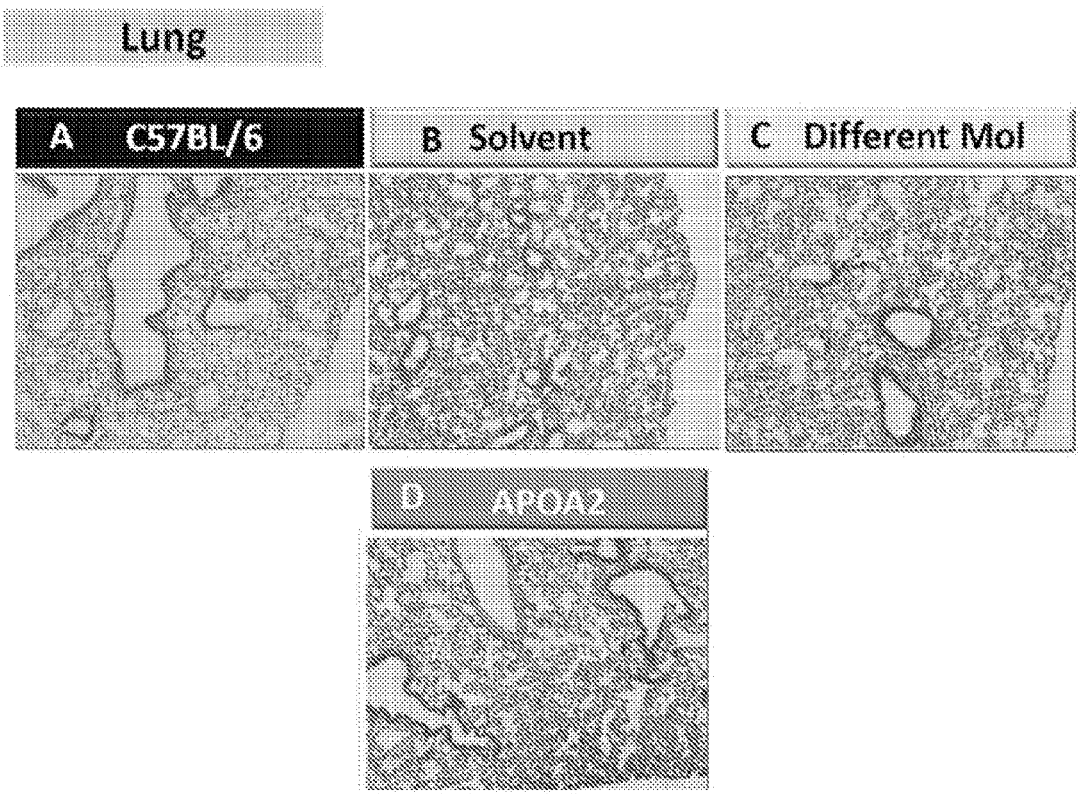
FIG. 11 A microscope photograph showing the results of evaluation of the therapeutic effect of anti-APOA2 polyclonal antibody on lung tissues in Embodiment 4.

Since intractable vasculitis is an autoimmune disease, microscopic images of lungs, which are affected organs as well as kidneys, were examined. In the untreated group and the Different Mol group of SCG/Kj model mice, vasculitis, hemorrhage, and granulation appeared in part in the lung tissue (FIGS. 11B and 11C). On the other hand, administration of the anti-APOA2 polyclonal antibody improved the lung tissue close to normal (FIGS. 11A and 11D).

Embodiment 5

5. Construction of hScFv Recombinants (VasAP) for the Therapy of Intractable Vasculitis 5-1. Construction of Recombinants 5-1-1) Protein expression by expression optimization in *E. coli*

In the preparation of a library of artificial gamma globulins according to patent literature 3 (Japanese Patent Application Laid-Open No. 2013-147495), the issue was to minimize the toxicity of gamma globulin to bacteria *E. coli* as much as possible. To solve this issue, the present inventors employed a pBAD vector which inserts foreign genes under the control of arabinose promoter as a vector that strictly controls protein expression by the plasmid. Thereafter, since an effective clone (VasSF) was selected from the above-mentioned library in patent literature 5 (Japanese Patent Application Laid-Open No. 2016-160265), search for a vector and sequence optimization for good expression efficiency by single clone were conducted.

5-1-2) Optimization of Protein Expression in *E. coli* (Introduction into pTAC-2 Vector)

Figure 12:
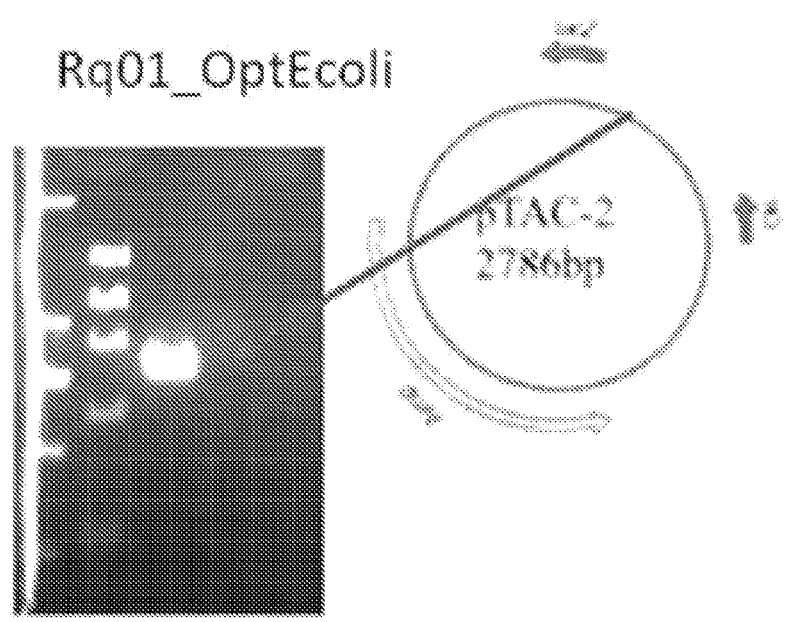
FIG. 12 Figure for explaining the plasmid ptac2-URq01_OptE.coli prepared in Embodiment 5.

Considering the codon usage of *E. coli* from the amino acid sequence of an effective clone (VasSF) (identical to SEQ ID NO: 4, and SEQ ID NO: 31 of patent literature 5) in order to maximize the expression efficiency of protein by *E. coli*, a plasmid pTAC2-URq01 Opt*Ecoli* containing an artificially synthesized gene (URq01 Opt*Ecoli* sequence; SEQ ID NO: 3) to which six histidine tags were added at the C-terminal was constructed (FIG. 12).

5-1-3) Introduction to pET32 Vector

The pET-based vector, which is a vector generally used for the purpose of strong expression of recombinant proteins in *E. coli*, can be up-regulated by the T7 promoter under the control of the LacZ operon. Therefore, in this experiment, the present inventors attempted to introduce the URq01_Opt*Ecoli* sequence into a pET-based vector.

Specifically, first, the insert sequence (coding region: region of SEQ ID NO: 3) was PCR-amplified from the plasmid pTAC2-URq01 Opt*Ecoli* constructed above to prepare an integration fragment. The nucleotide sequences of the primers used for this preparation are as follows (underlined part is a sequence homologous to the end of the cloning site of the pET32 vector).

Figure 13:
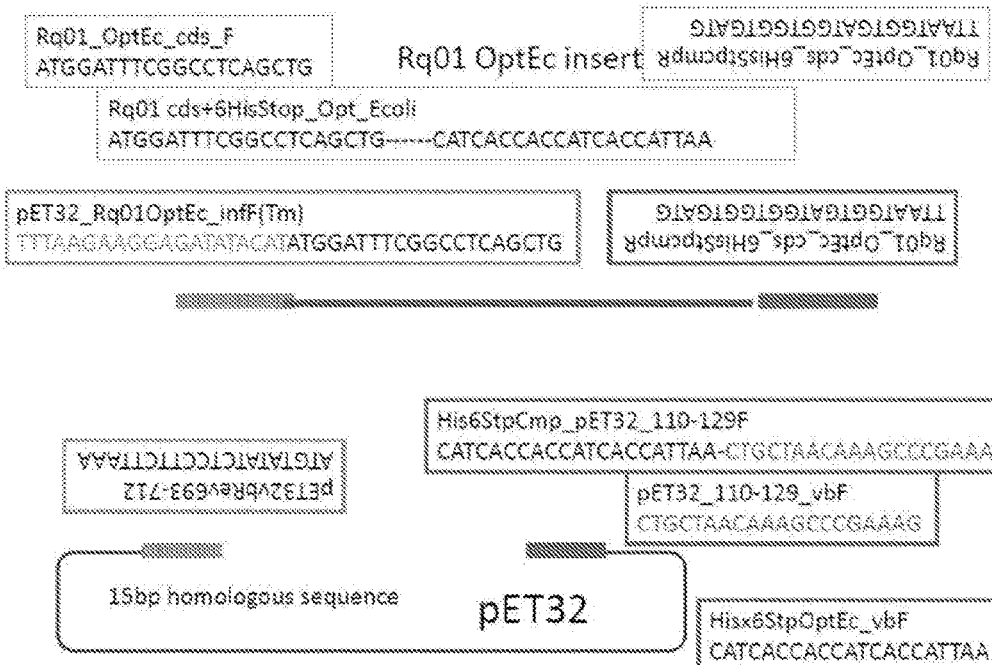
FIG. 13 Figure for explaining a method for incorporating the fragment containing a gene encoding an antibody in the invention a built-in a site where a T7 promoter control region of a pET32 vector in Embodiment 5. Sequences for upper part of FIG. 13: Rq01_OptEc_cds_F (SEQ ID NO: 9); Rg01 cds+6HisStop_Opt_Ecoli (5' portion) (SEQ ID NO: 9); Rq01 cds+6HisStop_Opt_Ecoli (3' portion) (SEQ ID NO:11); Rq01_OptEc_cds 6_HisStpcmpR (SEQ ID NO:6, shown twice); pET32_Rq01OptEc_infF(Tm) (SEQ ID NO:5). Sequences for lower part of FIG. 13: pET32vbRev693-712(SEQ ID NO:8); His6StpCmp_pET32_110-129F (SEQ ID NO:7); pET32_110-129_vbF (SEQ ID NO: 12); Hisx6StpOptEc_vbF (SEQ ID NO:11).

```
Forward primer:
TTTAAGAAGGAGATATACATATGGATTTCGGCCTCAGCTG
(SEQ ID NO: 5, pET32_Rq01OptEc_infF(Tm) in FIG.
13)
```

```
Reverse Primer:
TTAATGGTGATGGTGGTGATG
(SEQ ID NO: 6, Rq01_OptEc_cds_6HisStpcmpR in FIG.
13)
```

On the other hand, in order to linearize the pET32 vector and enable conjugation with the above-mentioned amplified fragment, the vector was amplified by performing inverse PCR. The nucleotide sequence of the primers used in this process are as follows (underlined part is a sequence homologous to the His-tag end of the insert sequence).

```
Forward primer:
CATCACCACCATCACCATTAACTGCTAACAAAGCCCGAAAG
(SEQ ID NO: 7, pET32vbRev693-712 in FIG. 13)
```

```
Reverse primer:
ATGTATATCTCCTTCTTAAA
(SEQ ID NO: 8, pET32vbRev693-712 in FIG. 13)
```

Figure 14:
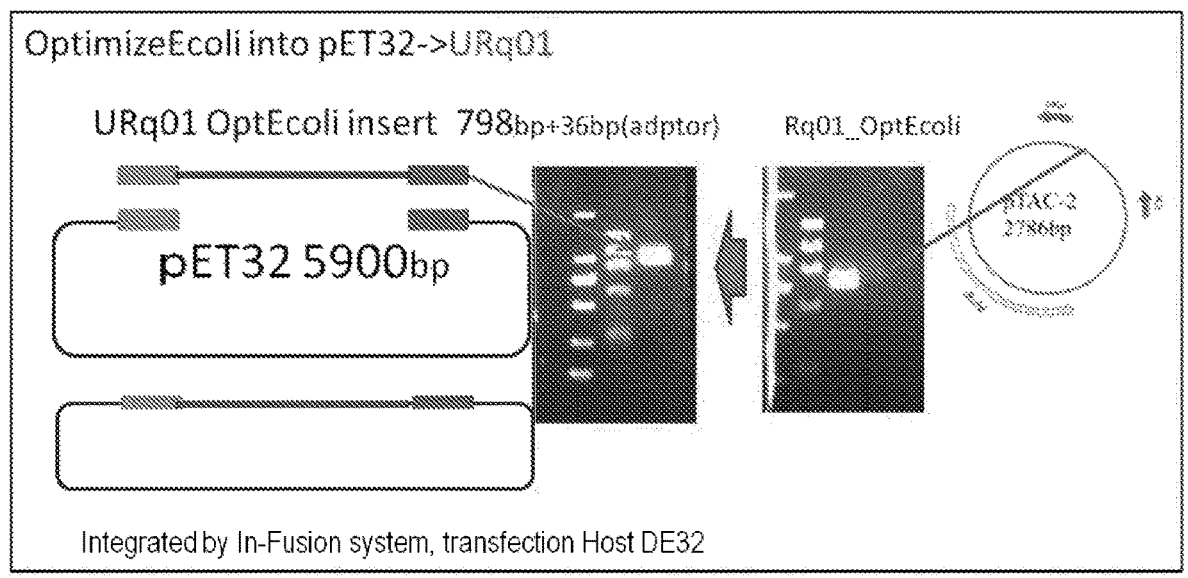
FIG. 14 Figure for explanatory diagram for explaining the whole operation in Embodiment 5.

The integration fragment and the linearized pET32 vector amplified above were fused using the In-Fusion® method (a ligation-independent method for cloning of PCR products; Takara Bio) to integrate the integration fragment at the integration site of the T7 promoter control region of the pET32 vector (FIG. 14).

Thereafter, a transformant was prepared by introducing the above vector into *E. coli* host DE32 using a heat shock method. The insertion sequence was confirmed from 10 colonies by PCR amplification of the insertion sequence using a primer set in the frame T7 promoter region of the pET32 vector and a primer in the T7 terminator region. The nucleotide sequences of the primers used in this process are as follows.

```
Forward primer:
ATGGATTTCGGCCTCAGCTG
(SEQ ID NO: 9, Rq01_OptEc_cds_F in FIG. 13)
```

```
Primer:
TTAATGGTGATGGTGGTGATG
(SEQ ID NO: 6, Rq01_OptEc_cds_6HisStpcmpR in
FIG. 13)
```

Then, all the clones were confirmed to be correctly constructed integration sequences by the determination of the sequence of plasmid DNA obtained from the 10 colonies.

5-2) Purification of Recombinant Clones

The recombinant protein (composed of SEQ ID NO: 4, also referred to herein as "VasAP") was purified from the culture of host *E. coli* DE32 by the following procedure. However, in the present invention, protein purification can be carried out using a general purification method. Examples of the purification method include immobilized metal ion affinity chromatography, fractionation with an ion exchange column, chromatography with a positive ion exchange resin such as DEAE, and gel filtration.

1) *E. coli* containing a target clone was cultured at 10° C. for 18 to 48 hours.

2) Bacterial cells were collected from culture solution of *E. coli* by centrifugation at 3,500×g for 30 minutes.

3) A solution of 20 mL of 6 M guanidine thiocyanate in 50 mM Tris buffer (pH 8.0) was added per bacterial cells from 1L of culture solution, and the cells were disrupted by sonication at 19 to 22 kHz three times for 15 seconds.

4) The supernatant was collected from sonicated bacterial solution by the centrifugation at 15,000×g. for 30 minutes.

5) From the supernatant, the peak fraction of hScFv (VasAP) derived from the target clone was collected by purification using immobilized metal ion affinity chromatography with 8 M Urea base.

6) Proteins isolated by Immobilized metal ion (Ni) affinity chromatography with 8 M urea base was centrifugally concentrated with an ultrafiltration membrane 10 kDa.

7) The peak fraction of the centrifugally concentrated protein was separated by gel filtration HPLC.

8) A peak fraction of the protein obtained by gel filtration HPLC was additionally purified by immobilized metal (Co) ion affinity chromatography.

9) Solution purified by immobilized metal (Co) ion affinity chromatography with 8M urea base was centrifugally concentrated with ultrafiltration membrane 10 kDa 10) Buffer containing the centrifugally concentrated protein was substituted to 8 M urea PBS buffer using gel filtration HPLC.

11) After buffer of the protein was exchanged into 8 M urea PBS buffer, the buffer was replaced with PBS by gradual reduction of the urea concentration by dialysis with addition of arginine. Specifically, the dialysis was performed in this order with 8M urea PBS, 4M urea/0.4M arginine, 2M urea/0.4M arginine, 2M urea 0.4M arginine, and PBS three times.

Figure 15:
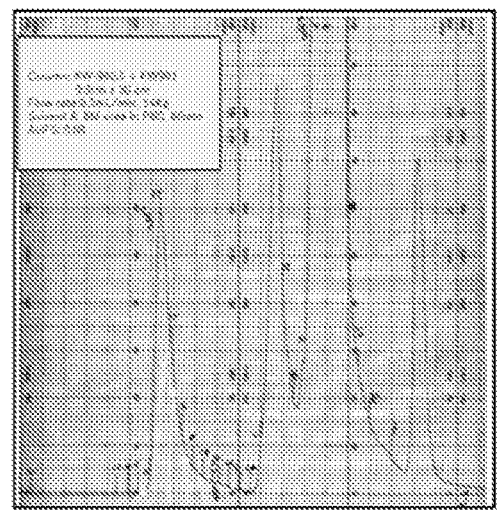
FIG. 15 Figure for results in purification of the recombinant protein (VasAP) from the culture of E. coli cells DE32) in Embodiment 5.
Figure 15:
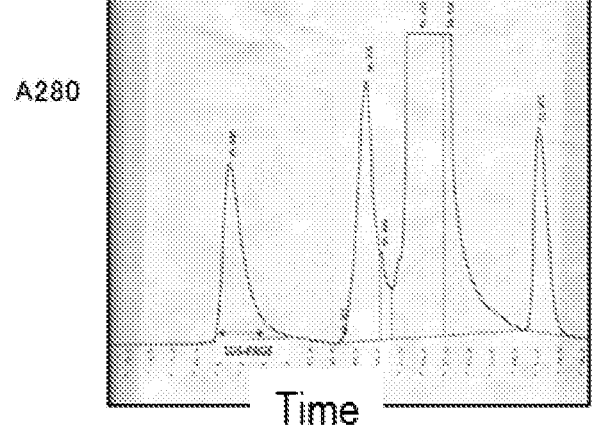
Figure 15:
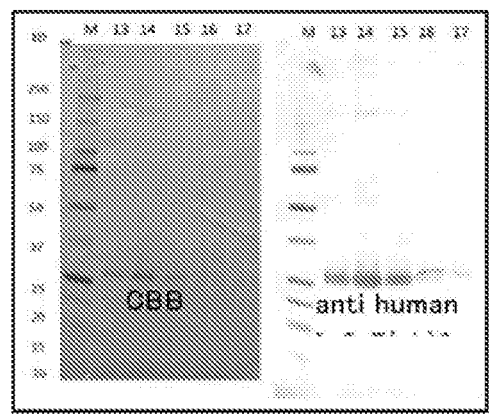

The results of the above purification are shown in FIG. 15. FIGS. 15A and 15B are photographs showing the results of gel filtration HPLC profiles, and FIG. 15C is a photograph showing the results of electrophoresis and Western blotting.

Embodiment 6

6. Confirmation of Therapeutic Effect of Monoclonal Recombinant VasAP Antibody
6-1. Therapeutic Effect of Recombinant VasAP Antibody on Rescent Formation in Glomeruli and Urinary Findings Using the recombinant VasAP antibody obtained above, the effect of the antibody on crescent formation in kidney glomeruli and urinary findings was confirmed using the SCG/Kj model mice in the same manner as in Embodiment 4 described above. The results are shown in FIG. 16.

Figure 16:
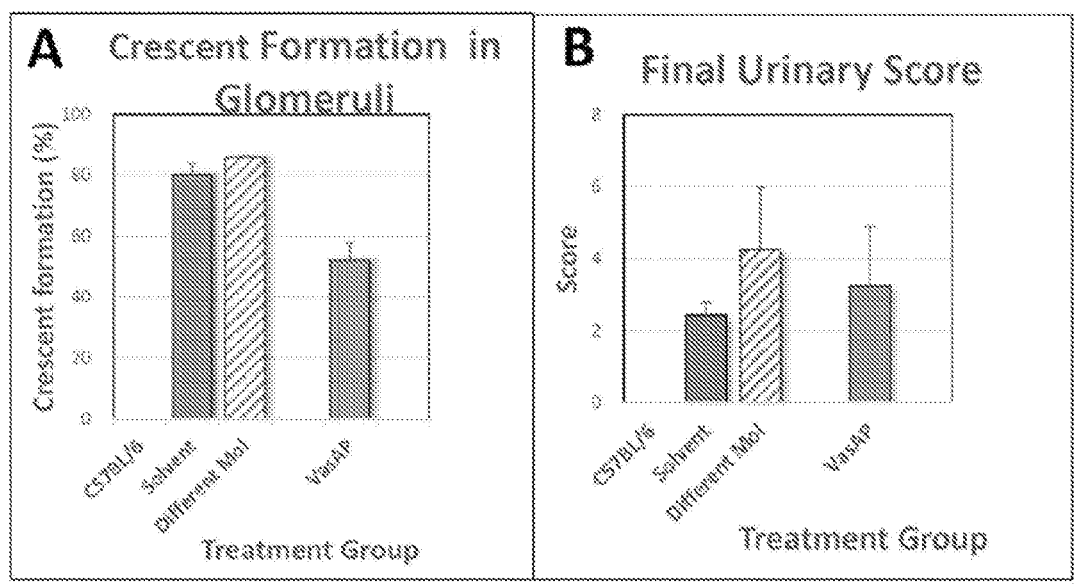
FIG. 16 Figure for results in evaluation of the therapeutic effect on the rate of crescent formation in kidney glomeruli by treatment with anti-APOA2 monoclonal antibody (VasAP) in Embodiment 6.

As shown in FIG. 16, administration of the VasAP antibody improved crescent formation in the SCG/Kj model mice (FIG. 16A), and urinary findings of antibody-treated mice showed lower values compared to ones of Different Mol treated mice (FIG. 16B).

6-2. Therapeutic Effect of Recombinant VasAP Antibody on Spleen Weight

Using the recombinant VasAP antibody obtained above and by the same method as in Embodiment 4, the effect of the antibody on spleen weight using SCG/Kj model mice was confirmed. The results are shown in FIG. 17.

Figure 17:
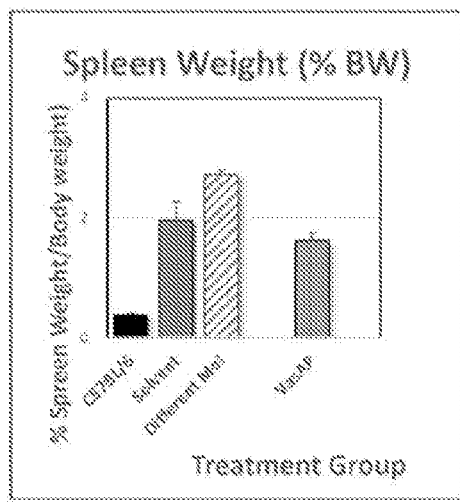
FIG. 17 Figure for results in evaluation of the therapeutic effect on weight of spleen by treatment with anti-APOA2 monoclonal antibody (VasAP) in Embodiment 6.

As shown in FIG. 17, the weight of enlarged spleen in SCG/Kj model mice was aggravated by administration of the Different Mol., but administration of the VasAP antibody decreased spleen weight.

6-3. Therapeutic effect of recombinant VasAP antibody on serum levels of biomarkers: MPO-ANCA and anti-moesin antibody Using the recombinant VasAP antibody obtained above and by the same method as in Embodiment 4, the effect of the antibody on serum levels of biomarkers: MPO-ANCA and anti-moesin antibody was confirmed using SCG/Kj model mice. The results are shown in FIG. 18.

Figure 18:
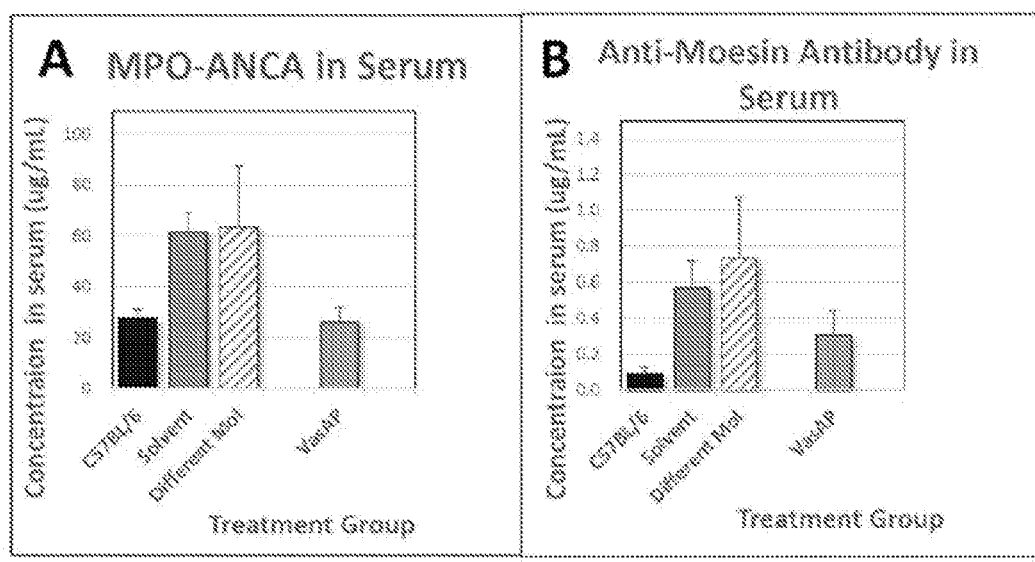
FIG. 18 Figure for results in evaluation of the therapeutic effect on serum levels of MPO-ANCA and anti-moesin antibody by treatment with anti-APOA2 monoclonal antibody (VasAP) in Embodiment 6.

As shown in FIG. 18, the levels of MPO-ANCA and anti-moesin antibody increased in SCG/Kj model mice was aggravated by administration of the Different Mol., but administration of the VasAP antibody improved them.

6-4. Therapeutic effect of recombinant VasAP antibody on serum levels of inflammatory cytokines and chemokines Using the recombinant VasAP antibody obtained above and by the same method as in Embodiment 4, the effect of the antibody on serum levels of inflammatory cytokines and chemokines was confirmed using SCG/Kj model mice. The results are shown in FIG. 19.

Figure 19:
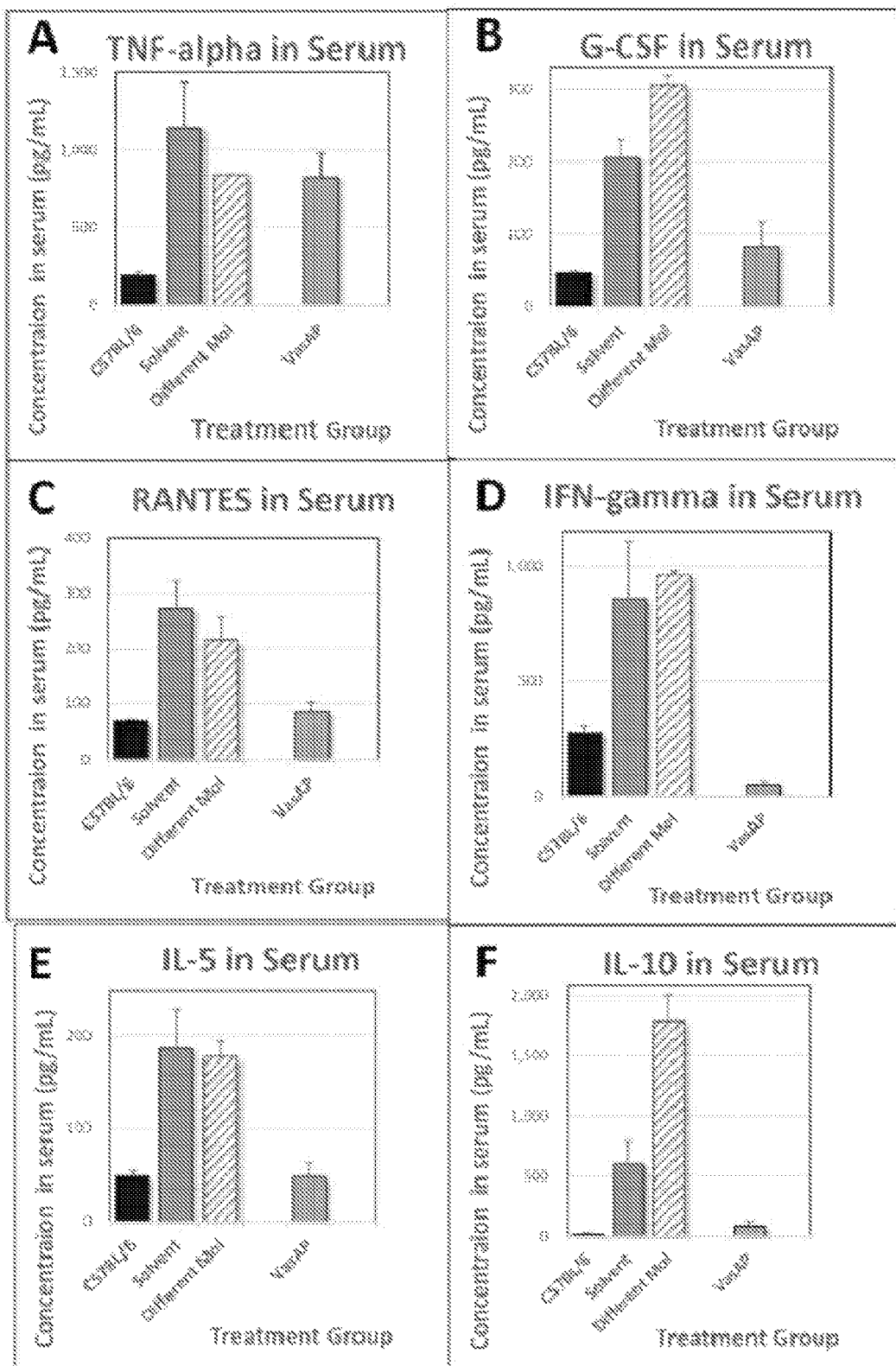
FIG. 19 Figure for results in evaluation of the therapeutic effect on serum levels of cytokines and chemokines by treatment with anti-APOA2 monoclonal antibody (VasAP) in Embodiment 6.

As shown in FIG. 19, administration of VasAP antibody decreased the serum levels of TNF-alpha, G-CSF, RANTES, IFN-gamma, IL-5, and IL-10, indicating the efficacy.

6-5. Therapeutic effect of recombinant VasAP antibody on white blood cell counts in the peripheral blood Using the recombinant VasAP antibody obtained above and by the same method as in Embodiment 4, the effect of the antibody on white blood cell counts in the peripheral blood was confirmed using SCG/Kj model mice. The results are shown in FIG. 20.

Figure 20:
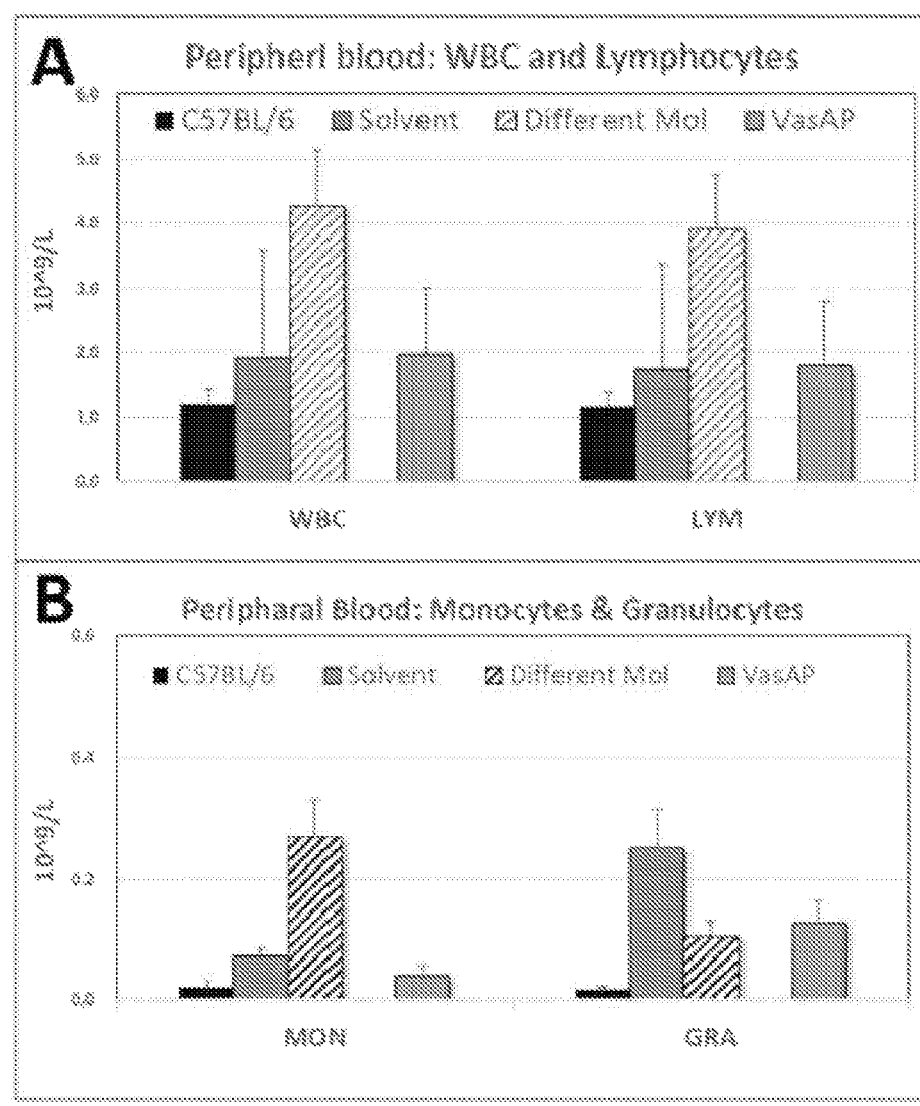
FIG. 20 Figure for results in evaluation of the therapeutic effect on cell counts in the peripheral blood by treatment with anti-APOA2 monoclonal antibody (VasAP) in Embodiment 6.

As shown in FIG. 20, administration of VasAP antibody did not significantly improve whole white blood cell counts (WBC), lymphocytes (LYM) (FIG. 20A), but the numbers of monocytes (MON) and neutrophils (GRA) reduced to nearly the value of the healthy mice (FIG. 20B).

Embodiment 7

7. Preparation and Evaluation of Induced Intractable Vasculitis Model Mice by Induction of Intractable Vasculitis in Wild-Type Mice
7-1. Induction of Vasculitis by Administration of APOA2 Protein
7-1-1) Test Animals Four female BALB/cCR mice (10-week old) were prepared. Three of them were assigned to experimental group and one to control group.

7-1-2) Preparation of Test Solution

APOA2 protein (BTI: BT-928, lot: 9280413) was prepared for this embodiment. The protein (1 mg) was dissolved in 1 ml of saline (#412190, produced by Nippon Pharmaceutical Industry Co. Ltd.). After addition of 1 ml of the saline solution, the protein solution was uniformly mixed to prepare 0.5 mg/mL test solution.

7-1-3) Administration of the Test Solution

The test solution prepared above were intraperitoneally administered to three mice of the experimental group (0.2 ml per mice; the dose of the test protein was 0.1 mg per mouse). On the other hand, in the control group, 0.2 ml of saline (solvent) was administered.

Figure 21:
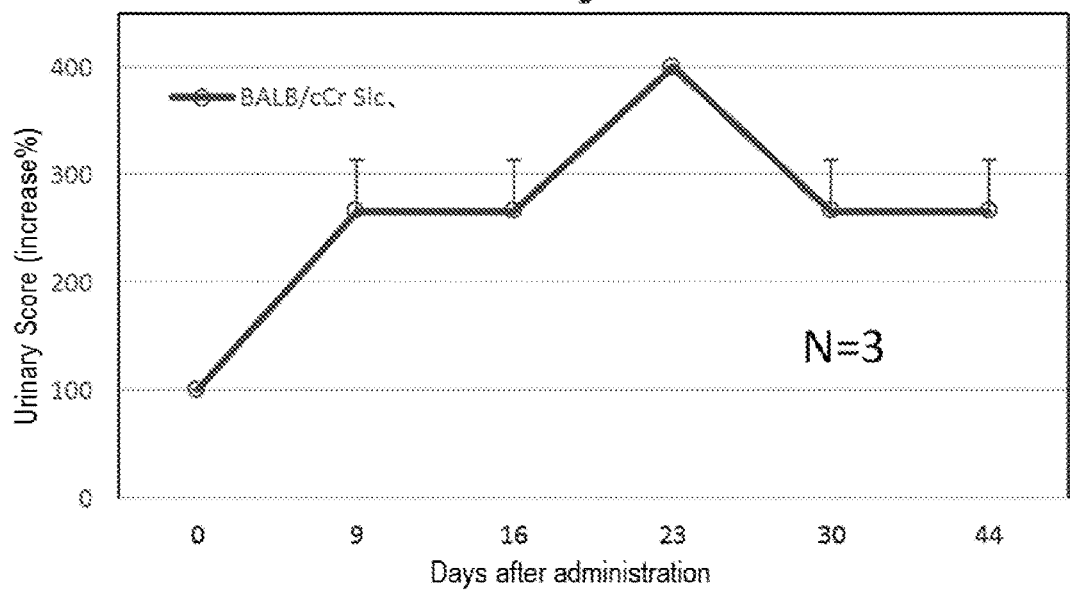
FIG. 21 Graph of results in daily evaluation of the urinary score in wild-type mice after administration of APOA2 protein in Embodiment 7.

7-2. Confirmation of Vasculitis Induction in Wild-Type Mice
7-2-2) Evaluation of Urinary Score Three mice of the experimental group administered with the above-described test solution were evaluated by urinary score up to 44 days after the administration of test solution (containing a test protein). The results are shown in FIG. 21. The graph shown in FIG. 21 is a relative value when the value on the day of administration (day 0) is 100 as the change in urinary scores (vertical axis; arithmetic mean value of 3 animals) with respect to days after administration (horizontal axis).

7-2-3) Confirmation of Crescent Formation in Kidney Glomeruli

Figure 22:
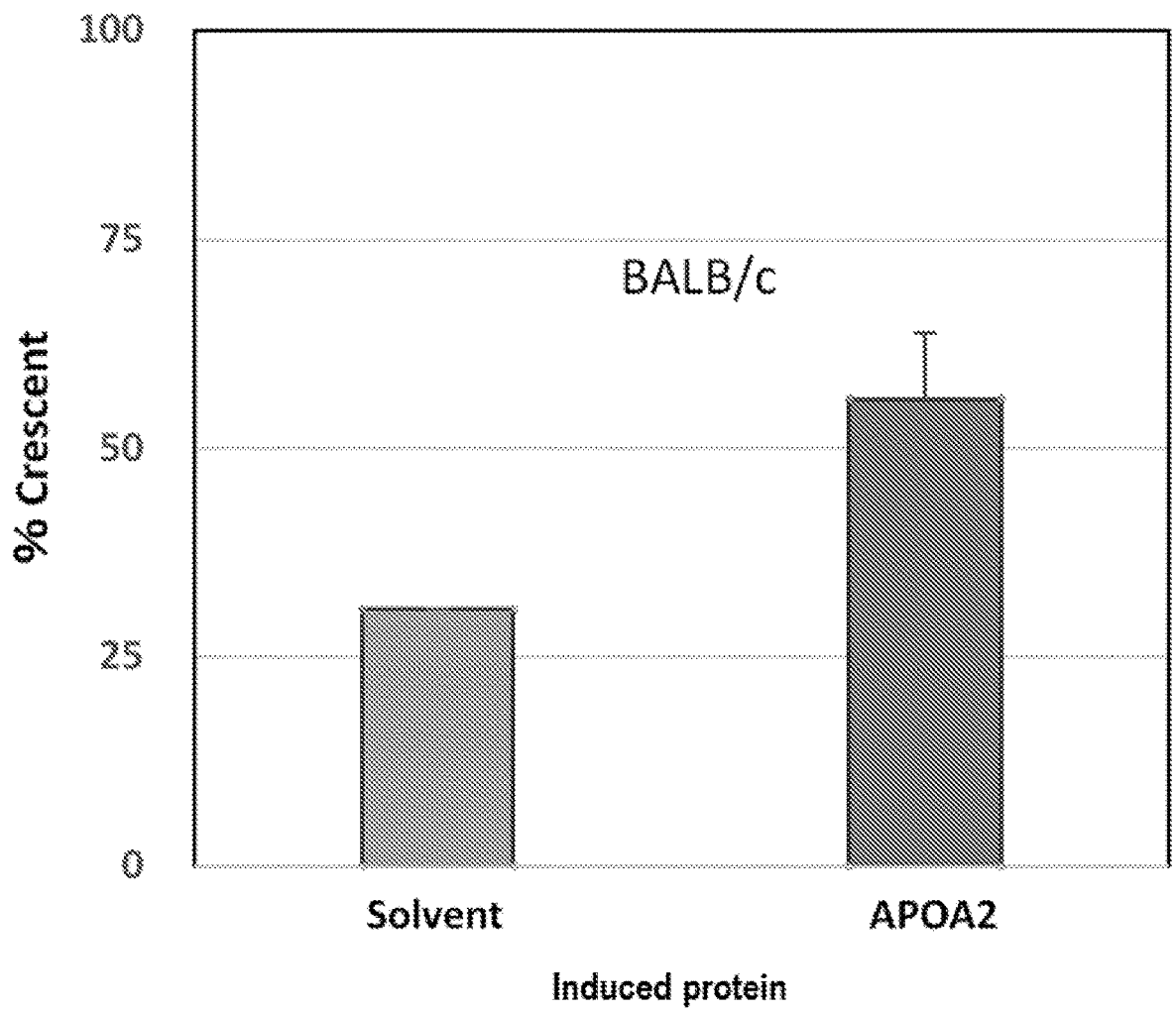
FIG. 22 Graph of results in the rate of crescent formation in kidney glomeruli in wild-type mice by administration of APOA2 protein in Embodiment 7.
Figure 23:
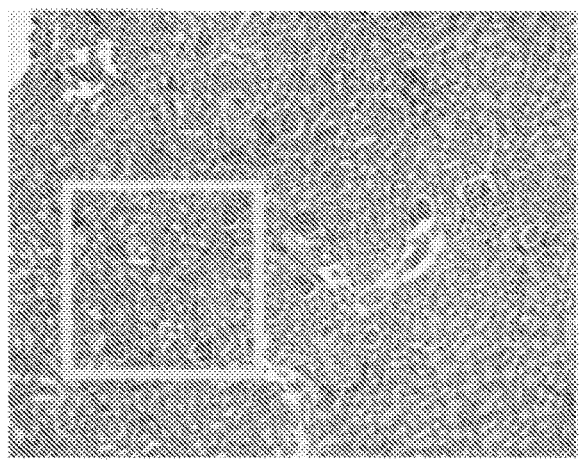
FIG. 23 Photograph of microscope in kidney tissues of wild-type mouse by administration of APOA2 protein in Embodiment 7.
Figure 23:
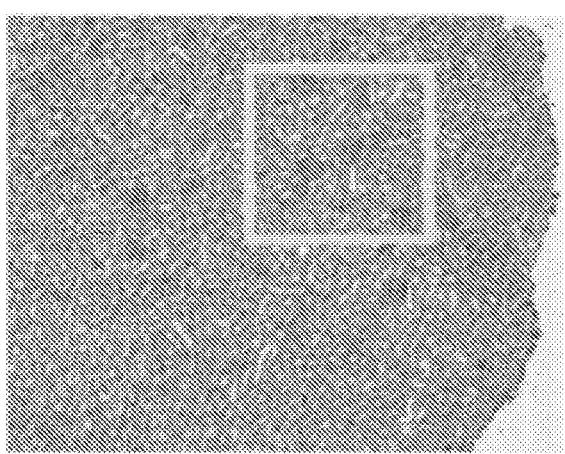
Figure 23:
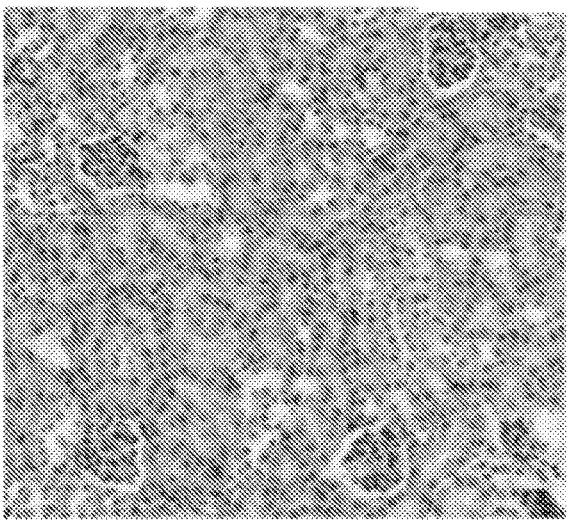
Figure 23:
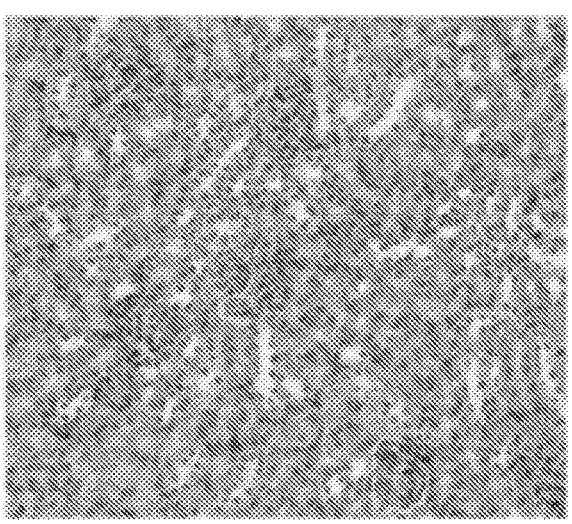

The crescent formation in the kidney glomeruli of each mouse was confirmed by calculating the crescent formation rate in the same manner as in Embodiment 4 described above for each of the control group and the experimental group. The results are shown in FIG. 22. In addition, the kidney tissue of each mouse was observed in the same manner as in Embodiment 4 described above to confirm formation of crescents. The results are shown in FIG. 23.

7-2-4) Observation of Microscopic Images of Spleen Tissues and Pulmonary Tissues The spleen tissue and lung tissue of each mouse were observed in the same manner as in Embodiment 4 described above. The results are shown in FIG. 23.

7-3. Results

As shown in FIG. 21, in the mice of the experimental group, the value of the urinary score increased with time after administration of the test protein (APOA2), and the value remained high thereafter. From this, it has been confirmed that administration of the test protein (APOA2) induces an inflammatory disease in mice of the experimental group.

In addition, as shown in FIG. 22, in the mice of the experimental group, the crescent formation rate in the kidney glomeruli was significantly increased as compared to the mice of the control group. Further, also in the microscopic image shown in FIG. 23, the microscopic image of the kidney glomeruli of the mice of the experimental group formed crescents, and renal dysfunction occurred. The "enlarged view" in the lower part of FIG. 23 is an enlarged view of a square-enclosed portion of the microscope image in the upper part.

Figure 24:
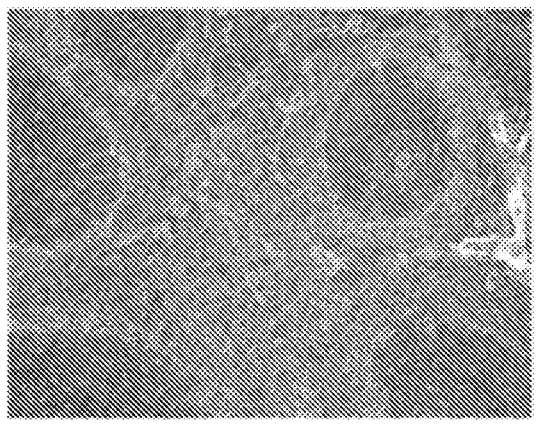
FIG. 24 Photograph of microscope in spleen and lung tissues of wild-type mouse by administration of APOA2 protein in Embodiment 7.
Figure 24:
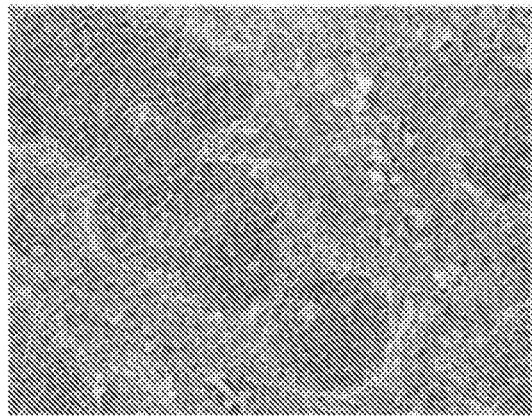
Figure 24:
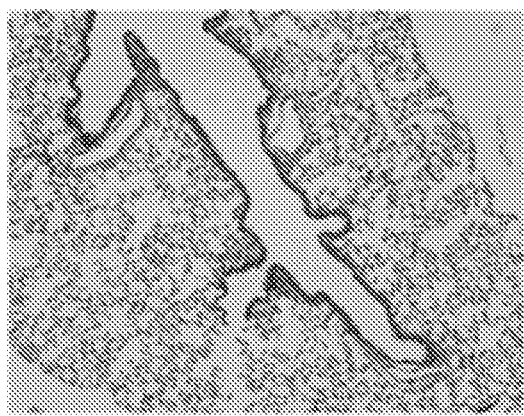
Figure 24:
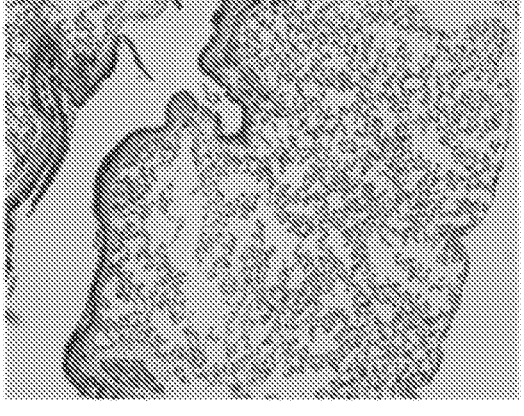

Furthermore, as shown in FIG. 24, while the microscopic images of the spleens of the mice in the control group show clear separation of white and red pulps, the microscopic images of the spleens of the mice in the experimental group show no separation of both pulps. Also, in the lung tissue of the experimental group mice, vasculitis, hemorrhage and granulation appeared in part, but in the control group mice these symptoms were not confirmed.

From the above, it was shown that an inflammatory disease (here, vasculitis) can be induced by administering APOA2 protein to a wild-type non-human animal (here, mouse).

[Sequence-free text]

The sequence id numbers (SEQ ID NO.) in the sequence table of the present specification show the following sequences.

[SEQ ID NO: 1]

The nucleotide sequence of DNA encoding human APOA2 (containing CDS and termination codon).

[SEQ ID NO: 2]

Amino acid sequence of human APOA2.

[SEQ ID NO: 3]

The nucleotide sequence of DNA encoding one (VasAP) of the antibodies in the present invention (including CDS and a termination codon).

[SEQ ID NO: 4]

An amino acid sequence of one (VasAP) of the antibodies in the present invention.

[SEQ ID NO: 5]

The nucleotide sequence of a PCR primer (pET32_Rq01OptEc_infF(Tm)).

[SEQ ID NO: 6]

The nucleotide sequence of a PCR primer (Rq01_OptEc_cds_6HisStpcmpR).

[SEQ ID NO: 7]

The nucleotide sequence of a PCR primer (His6StpCmp_pET32_110-129F).

[SEQ ID NO: 8]

The nucleotide sequence of a PCR primer (pET32vbRev693-712).

[SEQ ID NO: 9]

The nucleotide sequence of a PCR primer (Rq01_OptEc_cds_F).

This application is based on Japanese Patent Application No. 2017-13486 filed on Jan. 27, 2017, the disclosure of which is incorporated in its entirety by reference.

The invention claimed is:

1. A method of detecting a prophylactic and/or therapeutic agent for vasculitis in a test substance, wherein the prophylactic and/or therapeutic agent inhibits the activity or reduces expression of APOA2, the method comprising:
   (a) comparing the activity of isolated apolipoprotein A2 (APOA2) in the presence and absence of the test substance, or culturing cells having the ability to produce APOA2 in the presence and absence of the test substance and then comparing the activity of the APOA2 under both conditions;
   (b) detecting that the activity of APOA2 is inhibited or the expression of APOA2 is reduced in the presence of the test substance, thereby detecting that the prophylactic and/or therapeutic agent is present in the test substance.

2. The method according to claim 1, wherein the cells having the ability to produce APOA2 have been transfected with a nucleic acid encoding the APOA2.

3. The method according to claim 1, wherein the test substance comprises proteins, peptides, non-peptide compounds, synthetic compounds, fermentation products, cell extracts, plant extracts, animal tissue extracts, or combinations thereof.

4. The method according to claim 1, wherein the method comprises using a screening kit comprising APOA2 or a portion thereof to detect the prophylactic and/or therapeutic agent for vasculitis.

5. The method according to claim 4, wherein the screening kit further comprises a reaction buffer, a blocking solution, a washing buffer, a labeling reagent, or a label detection reagent.

6. The method according to claim 1, wherein the method comprises using a screening kit comprising an antibody specifically binding APOA2 to detect the prophylactic and/or therapeutic agent for vasculitis, wherein the antibody specifically binding APOA2 is for measuring the expression amount of APOA2 in the cells producing the APOA2.

7. The method according to claim 6, wherein the screening kit further comprises a reaction buffer, a blocking solution, a washing buffer, a labeling reagent, or a label detection reagent.

* * * * *

SEQUENCE LISTING

```
<160> NUMBER OF SEQ ID NOS: 12

<210> SEQ ID NO 1
<211> LENGTH: 303
<212> TYPE: DNA
<213> ORGANISM: Homo sapiens
<220> FEATURE:
<221> NAME/KEY: misc_feature
<223> OTHER INFORMATION: Coding DNA sequence for human APOA2

<400> SEQUENCE: 1
atgaagctgc tcgcagcaac tgtgctactc ctcaccatct gcagccttga aggagctttg      60
gttcggagac aggcaaagga gccatgtgtg gagagcctgg tttctcagta cttccagacc     120
gtgactgact atggcaagga cctgatggag aaggtcaaga gcccagagct tcaggccgag     180
gccaagtctt actttgaaaa gtcaaggag cagctgacac ccctgatcaa gaaggctgga     240
acggaactgg ttaacttctt gagctatttc gtggaacttg aacacagcc tgccacccag     300 tga                                                                   303

<210> SEQ ID NO 2
<211> LENGTH: 100
<212> TYPE: PRT
<213> ORGANISM: Homo sapiens
<220> FEATURE:
<221> NAME/KEY: MISC_FEATURE
<223> OTHER INFORMATION: Amino acid sequence of human APOA2
```

<400> SEQUENCE: 2

Met Lys Leu Leu Ala Ala Thr Val Leu Leu Thr Ile Cys Ser Leu
1               5                   10                  15

Glu Gly Ala Leu Val Arg Arg Gln Ala Lys Glu Pro Cys Val Glu Ser
            20                  25                  30

Leu Val Ser Gln Tyr Phe Gln Thr Val Thr Asp Tyr Gly Lys Asp Leu
            35                  40                  45

Met Glu Lys Val Lys Ser Pro Glu Leu Gln Ala Glu Ala Lys Ser Tyr
50                  55                  60

Phe Glu Lys Ser Lys Glu Gln Leu Thr Pro Leu Ile Lys Lys Ala Gly
65                  70                  75                  80

Thr Glu Leu Val Asn Phe Leu Ser Tyr Phe Val Glu Leu Gly Thr Gln
                85                  90                  95

Pro Ala Thr Gln
            100

<210> SEQ ID NO 3
<211> LENGTH: 798
<212> TYPE: DNA
<213> ORGANISM: Artificial Sequence
<220> FEATURE:
<223> OTHER INFORMATION: DNA sequence coding VasAP antibody

<400> SEQUENCE: 3

```
atggatttcg gccttagctg gattttcctg gtagcgctgc tgcgtggcgt acagtgccaa    60
gtacacttag tggagtctgg tggtggcttg gttcaaccgg tcgttctctc tgcggctctca   120
tgtgcggtga gcggcttcac ctttgcgtcc tatgccatgc attgggtccg tcaggctcct   180
ggcaaagggc tggaatgggt cgcagggatc agtaaggatg ggagcaacaa acgtcatgcc   240
gatagcctcg aaggccgctt taccattagt cgcgataact cgaagaacac cctgtatctc   300
caggttagtg gcttacgcgc agaagatacc gccgtttact attgtgcgcg ctcacaagat   360
ccgacggact cgattggct tctgtccgaa cattgggtc agggtactct ggtgacagtc   420
tcgtcagcga gcacaaaagg cccgtcgtg tttccgttag ccccttgttc tgcagtact   480
tccgagagta ctgctgcact gggttgcctg gtgaaagact acttccccgga accggttacc   540
gtgtcgtgga attcaggtgc actgacctct ggagtccata cgtttcctgc ggttttgcag   600
tcgagcggct tgtactctct gagcagcgtt gtgacggtgc cgagctccaa ctttggaacc   660
cagacctata cgtgcaatgt ggatcacaaa ccctccaata cgaaggtaga caaaaccgtg   720
gctccaccag ttgccggtcc aagcgtcttt ctgtttccgc ccaaaccgaa agacacacat   780
caccaccatc accattaa                                                 798
```

<210> SEQ ID NO 4
<211> LENGTH: 265
<212> TYPE: PRT
<213> ORGANISM: Artificial Sequence
<220> FEATURE:
<223> OTHER INFORMATION: Amino acid sequence of VasAP antibody

<400> SEQUENCE: 4

Met Asp Phe Gly Leu Ser Trp Ile Phe Leu Val Ala Leu Leu Arg Gly
1               5                   10                  15

Val Gln Cys Gln Val His Leu Val Glu Ser Gly Gly Gly Leu Val Gln
            20                  25                  30

Pro Gly Arg Ser Leu Arg Leu Ser Cys Ala Val Ser Gly Phe Thr Phe

```
            35                  40                  45
Ala Ser Tyr Ala Met His Trp Val Arg Gln Ala Pro Gly Lys Gly Leu
 50                  55                  60

Glu Trp Val Ala Gly Ile Ser Lys Asp Gly Ser Asn Lys Arg His Ala
 65                  70                  75                  80

Asp Ser Leu Glu Gly Arg Phe Thr Ile Ser Arg Asp Asn Ser Lys Asn
                 85                  90                  95

Thr Leu Tyr Leu Gln Val Ser Gly Leu Arg Ala Glu Asp Thr Ala Val
             100                 105                 110

Tyr Tyr Cys Ala Arg Ser Gln Asp Pro Thr Asp Phe Asp Trp Leu Leu
         115                 120                 125

Ser Glu His Trp Gly Gln Gly Thr Leu Val Thr Val Ser Ser Ala Ser
     130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Ala Pro Pro Val Ala Gly Pro Ser Val Phe Leu Phe Pro Pro Lys Pro
                245                 250                 255

Lys Asp Thr His His His His His His
            260                 265

<210> SEQ ID NO 5
<211> LENGTH: 40
<212> TYPE: DNA
<213> ORGANISM: Artificial Sequence
<220> FEATURE:
<223> OTHER INFORMATION: Base sequence for PCR primer
      (pET32_Rq01OptEc_infF(Tm))

<400> SEQUENCE: 5
tttaagaagg agatatacat atggatttcg gcctcagctg                           40

<210> SEQ ID NO 6
<211> LENGTH: 21
<212> TYPE: DNA
<213> ORGANISM: Artificial Sequence
<220> FEATURE:
<223> OTHER INFORMATION: Base sequence for PCR primer
      (Rq01_OptEc_cds_6HisStpcmpR)

<400> SEQUENCE: 6
ttaatggtga tggtggtgat g                                               21

<210> SEQ ID NO 7
<211> LENGTH: 41
<212> TYPE: DNA
<213> ORGANISM: Artificial Sequence
<220> FEATURE:
<223> OTHER INFORMATION: Base sequence for PCR primer
      (His6StpCmp_pET32_110-129F)
```

```
<400> SEQUENCE: 7
catcaccacc atcaccatta actgctaaca aagcccgaaa g                41

<210> SEQ ID NO 8
<211> LENGTH: 20
<212> TYPE: DNA
<213> ORGANISM: Artificial Sequence
<220> FEATURE:
<223> OTHER INFORMATION: Base sequence for PCR primer
      (pET32vbRev693-712)

<400> SEQUENCE: 8
atgtatatct ccttcttaaa                                        20

<210> SEQ ID NO 9
<211> LENGTH: 20
<212> TYPE: DNA
<213> ORGANISM: Artificial Sequence
<220> FEATURE:
<223> OTHER INFORMATION: Base sequence for PCR primer (Rq01_OptEc_cds_F)

<400> SEQUENCE: 9
atggatttcg gcctcagctg                                        20

<210> SEQ ID NO 10
<211> LENGTH: 265
<212> TYPE: PRT
<213> ORGANISM: Homo sapiens

<400> SEQUENCE: 10
```

Met Asp Phe Gly Leu Ser Trp Ile Phe Leu Val Ala Leu Leu Arg Gly
1               5                   10                  15

Val Gln Cys Gln Val His Leu Val Glu Ser Gly Gly Gly Leu Val Gln
            20                  25                  30

Pro Gly Arg Ser Leu Arg Leu Ser Cys Ala Val Ser Gly Phe Thr Phe
        35                  40                  45

Ala Ser Tyr Ala Met His Trp Val Arg Gln Ala Pro Gly Lys Gly Leu
    50                  55                  60

Glu Trp Val Ala Gly Ile Ser Lys Asp Gly Ser Asn Lys Arg His Ala
65                  70                  75                  80

Asp Ser Leu Glu Gly Arg Phe Thr Ile Ser Arg Asp Asn Ser Lys Asn
                85                  90                  95

Thr Leu Tyr Leu Gln Val Ser Gly Leu Arg Ala Glu Asp Thr Ala Val
            100                 105                 110

Tyr Tyr Cys Ala Arg Ser Gln Asp Pro Thr Asp Phe Asp Trp Leu Leu
        115                 120                 125

Ser Glu His Trp Gly Gln Gly Thr Leu Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

```
Cys Asn Val Asp His Lys Pro Ser Asn Thr Lys Val Asp Lys Thr Val
225                 230                 235                 240

Ala Pro Pro Val Ala Gly Pro Ser Val Phe Leu Phe Pro Pro Lys Pro
                245                 250                 255

Lys Asp Thr His His His His His His
                260                 265

<210> SEQ ID NO 11
<211> LENGTH: 21
<212> TYPE: DNA
<213> ORGANISM: Artificial Sequence
<220> FEATURE:
<223> OTHER INFORMATION: Rq01 cds+6HisStop_Opt_Ecoli (3' portion)

<400> SEQUENCE: 11
catcaccacc atcaccatta a                                         21

<210> SEQ ID NO 12
<211> LENGTH: 20
<212> TYPE: DNA
<213> ORGANISM: Artificial Sequence
<220> FEATURE:
<223> OTHER INFORMATION: Base sequence for PCR primer
      (pET32_110-129_vbF)

<400> SEQUENCE: 12
ctgctaacaa agcccgaaag                                           20
```